(12) United States Patent
Nagashima et al.

(10) Patent No.: US 11,246,299 B2
(45) Date of Patent: Feb. 15, 2022

(54) DISEASE MODEL PIG EXHIBITING STABLE PHENOTYPE, AND PRODUCTION METHOD THEREOF

(71) Applicant: PorMedTec Co., Ltd., Kanagawa (JP)

(72) Inventors: Hiroshi Nagashima, Kanagawa (JP); Hitomi Matsunari, Kanagawa (JP); Masahito Watanabe, Kanagawa (JP)

(73) Assignee: PorMedTec Co., Ltd., Kanagawa (JP)

( * ) Notice: Subject to any disclaimer, the term of this patent is extended or adjusted under 35 U.S.C. 154(b) by 776 days.

(21) Appl. No.: 15/553,934

(22) PCT Filed: Mar. 4, 2016

(86) PCT No.: PCT/JP2016/056865
§ 371 (c)(1),
(2) Date: Dec. 29, 2017

(87) PCT Pub. No.: WO2016/140353
PCT Pub. Date: Sep. 9, 2016

(65) Prior Publication Data
US 2018/0103619 A1   Apr. 19, 2018

(30) Foreign Application Priority Data
Mar. 4, 2015   (JP) .............................. JP2015-041923

(51) Int. Cl.
*A01K 67/027* (2006.01)
*C12N 9/10* (2006.01)
*C07K 14/705* (2006.01)
*C07K 14/47* (2006.01)
*C12N 5/16* (2006.01)
*C12N 15/877* (2010.01)

(52) U.S. Cl.
CPC ........ *A01K 67/0275* (2013.01); *A01K 67/027* (2013.01); *A01K 67/0271* (2013.01); *A01K 67/0273* (2013.01); *A01K 67/0276* (2013.01); *C07K 14/4702* (2013.01); *C07K 14/705* (2013.01); *C12N 5/16* (2013.01); *C12N 9/1018* (2013.01); *C12N 15/8778* (2013.01); *C12Y 201/03003* (2013.01); *A01K 2227/108* (2013.01); *A01K 2267/0306* (2013.01); *A01K 2267/0362* (2013.01); *A01K 2267/0375* (2013.01)

(58) Field of Classification Search
CPC ............ A61K 67/0271; A61K 67/0275; A61K 67/0276; A61K 2227/108; A61K 2227/0306
See application file for complete search history.

(56) References Cited

U.S. PATENT DOCUMENTS

| 7,291,764 B1 | 11/2007 | Stice et al. |
|---|---|---|
| 2001/0029040 A1 | 10/2001 | Toyo-Oka |
| 2002/0010949 A1 | 1/2002 | Stice et al. |
| 2002/0035737 A1 | 3/2002 | Stice et al. |
| 2003/0177513 A1 | 9/2003 | Echelard et al. |
| 2005/0260176 A1 | 11/2005 | Ayares et al. |
| 2009/0271882 A1 | 10/2009 | Umeyama et al. |
| 2010/0122356 A1 | 5/2010 | Kragh et al. |
| 2010/0273199 A1 | 10/2010 | Turner et al. |
| 2013/0191931 A1 | 7/2013 | Grompe et al. |
| 2014/0096275 A1* | 4/2014 | Prather .............. A01K 67/0276 800/17 |
| 2014/0123330 A1 | 5/2014 | Carlson et al. |

FOREIGN PATENT DOCUMENTS

| JP | 2001-509362 A | 7/2001 |
|---|---|---|
| JP | 2001-231557 A | 8/2001 |
| JP | 2001-512964 A | 8/2001 |
| JP | 2002-238562 A | 8/2002 |
| JP | 2003-509031 A | 3/2003 |
| JP | 2003-510072 A | 3/2003 |
| JP | 2004-073189 A | 3/2004 |
| JP | 2007-82454 A | 4/2007 |
| JP | 2007-167078 A | 7/2007 |
| JP | 2008-121964 A | 5/2008 |
| JP | 2010-110254 A | 5/2010 |
| JP | 2010-520751 A | 6/2010 |
| JP | 2011-506922 A | 3/2011 |

(Continued)

OTHER PUBLICATIONS

Matsunari et al. Laboratory Investigation https://doi.org/10.1038/s41374-020-0406-7. pp. 1-13, 2020 (Year: 2020).*
Naito et al. J Reprod Fert 113:137-143, 1998 (Year: 1998).*
Dolatshad et al. Mammalian Genome 26:598-608, 2015 (Year: 2015).*
Yao et al. Scientific Reports 4:6926. DOI:10.1038/srep06926. Nov. 2014. pp. 1-8 (Year: 2014).*
Carlson et al. PNAS 109:17382-17387, 2012 (Year: 2012).*
Laible et al. Biotechnology Journal 10:109-120, 2015 (Year: 2015).*
Liu et al. Nature Communications Oct. 14, 2013, pp. 1-11 (Year: 2013).*
Gao et al. Genome Biology 18:1-15, 2017 (Year: 2017).*
Matsunari et al. PNAS 110(12):4557-4562, 2013 (Year: 2013).*
Matsuda et al. Cloning and Stem Cell 4(1):9-20, 2002 (Year: 2002).*

(Continued)

*Primary Examiner* — Marcia S Noble
(74) *Attorney, Agent, or Firm* — Oblon, McClelland, Maier & Neustadt, L.L.P.

(57) ABSTRACT

Disease model pigs produced by nuclear transplantation, disease model pigs exhibiting stable phenotypes and production methods thereof are provided. Chimeric pigs for producing disease model pigs exhibiting stable phenotypes, genital glands thereof, and germ cells thereof are also provided. A method for producing a genetically modified disease model pig, includes: (a) transplanting a nucleus of a genetically modified cell into cytoplasm of an egg; (b) developing an obtained clonal embryo in a womb of a female pig to obtain an offspring; and mating the obtained offspring or having the offspring undergo sexual reproduction to further obtain the genetically modified offspring as a disease model pig.

3 Claims, 6 Drawing Sheets

Specification includes a Sequence Listing.

(56) References Cited

FOREIGN PATENT DOCUMENTS

| JP | 2011-223976 A | 11/2011 |
|----|----|----|
| JP | 2011-229456 A | 11/2011 |
| JP | 2013-118859 A | 6/2013 |
| JP | 2013-215615 A | 10/2013 |
| JP | 2015-002719 A | 1/2015 |
| WO | 2000/026357 A2 | 5/2000 |
| WO | 2001/019181 A1 | 3/2001 |
| WO | 2001/023541 A2 | 4/2001 |
| WO | WO 2008/106984 A2 | 9/2008 |
| WO | 2014/085501 A1 | 6/2014 |
| WO | 2015/155904 A1 | 10/2015 |
| WO | 2016/029919 A1 | 3/2016 |

OTHER PUBLICATIONS

Cibeli et al. Theriogenology 49(1):236, 1998 (Year: 1998).*

Nagashima, H., et al., "Sex Differentiation and Germ Cell Production in Chimeric Pigs Produced by Inner Cell Mass Injection into Blastocysts", Biology of Reproduction, vol. 70, Nov. 12, 2003, pp. 702-707.

Matsunari, H., et al., "Transgenic-Cloned Pigs Systemically Expressing Red Fluorescent Protein, Kusabira-Orange", Cloning and Stem Cells, vol. 10, No. 3, 2008, pp. 313-323.

Umeyama, K., et al., "Dominant-Negative Mutant Hepatocyte Nuclear Factor 1α Induces Diabetes in Transgenic-Cloned Pigs", Transgenic Res, vol. 18, 2009, pp. 697-706.

Umeyama, K., et al., "Production of Diabetic Offspring Using Cryopreserved Epididymal Sperm by In Vitro Fertilization and Intrafallopian Insemination Techniques in Transgenic Pigs", Journal of Reproduction and Development, vol. 59, No. 6, 2013, pp. 599-603.

Davis, B. T., et al., "Targeted Disruption of LDLR Causes Hypercholesterolemia and Atherosclerosis in Yucatan Miniature Pigs", PLoS One, vol. 9, iss. 4, Apr. 2014, pp. 1-11.

Hickey, R. D., et al., "Fumarylacetoacetate Hydrolase Deficient Pigs are a Novel Large Animal Model of Metabolic Liver Disease", Stem Cell Res, vol. 13, No. 1, Jul. 2014, pp. 144-153 (submitting NIH Public Access Manuscript, 19 pages).

Matsunari, H., et al., "Significance of Blastocyst Complementation in Development of Genetically Modified Disease Model Pig: Rescue of Neonatal Lethality Genotype and Mediation to Gamogenesis", 108th Meeting of the Society for Reproduction and Development, Sep. 15, 2015, Session ID OR1-19.

International Search Report dated May 24, 2016, in PCT/ JP2016/ 056865, filed Mar. 4, 2016.

Towbin, et al., "Inherited Cardiomyopathies", Official Journal of the Japanese Circulation Society, 2014.

Schoensiegel, F., et al., "Atrial Natriuretic Peptide and Osteopontin are Useful Markers of Cardiac Disorders in Mice", Comparative Medicine, vol. 57, No. 6, Dec. 2007, pp. 546-553.

* cited by examiner

FIG.4

```
WT:   TAAGTATATCCTATGGCTATcagctgatctgaAATTTAGGATAAAGCAGAAA    (SEQ ID NO:18)

1:  TAAGTATATCCTATGGCTATcag********aAATTTAGGATAAAGCAGAAA    (SEQ ID NO: 19)
 10:  TAAGTATATCCTATGGCTATcagc******gaAATTTAGGATAAAGCAGAAA    (SEQ ID NO: 20)
 11:  TAAGTATATCCTATGGCTATcagctga*ctgaAATTTAGGATAAAGCAGAAA    (SEQ ID NO: 21)
 16:  TAAGTATATCCTATGGCTATcaA***atctgaAATTTAGGATAAAGCAGAAA    (SEQ ID NO: 22)
 22:  TAAGTATATCCTATGGCTATcagctga*ctgaAATTTAGGATAAAGCAGAAA    (SEQ ID NO: 23)
 38:  TAAGTATATCCTATG***********atctgaAATTTAGGATAAAGCAGAAA    (SEQ ID NO: 24)
 39:  TAAGTATATCCTATGGCTATcagcCA***tgaAATTTAGGATAAAGCAGAAA    (SEQ ID NO: 25)
 44:  TAAGTATATCCTATGGCTATcagcAGtgatctgaAATTTAGGATAAAGCAGAAA  (SEQ ID NO: 26)
 49:  TAAGTATATCCTATGGCTATc****gatctgaAATTTAGGATAAAGCAGAAA    (SEQ ID NO: 27)
 55:  TAAGTATATCCTATGGCTAT****************TTAGGATAAAGCAGAAA   (SEQ ID NO: 28)
 60:  TAAGTATATCCTATGGCTATcag***************GATAAAGCAGAAA     (SEQ ID NO: 29)
 69:  TAAGTATATCCTATGGCTATcagctga*****AATTTAGGATAAAGCAGAAA    (SEQ ID NO: 30)
 71:  TAAGTATATCCTAT***************gaAATTTAGGATAAAGCAGAAA     (SEQ ID NO: 31)
 73:  TAAGTATATCCTATGGCTATcaA***atctgaAATTTAGGATAAAGCAGAAA    (SEQ ID NO: 32)
 74:  TAAGTATATCCTATGGCT***********gaAATTTAGGATAAAGCAGAAA     (SEQ ID NO: 33)
 75:  TAAGTATATCCTATGGCT***********gaAATTTAGGATAAAGCAGAAA     (SEQ ID NO: 34)
 80:  TAAGTATATCCTATGGCTATcag*tgatctgaAATTTAGGATAAAGCAGAAA    (SEQ ID NO: 35)
 86:  TAAGTATATCCTATGGCTATcagct*atctgaAATTTAGGATAAAGCAGAAA    (SEQ ID NO: 36)
 89:  TAAGTATATCCTATGGCTATcagctga**gaAATTTAGGATAAAGCAGAAA     (SEQ ID NO: 37)
 90:  TAAGTATATCCTATGGCTATcag******gaAATTTAGGATAAAGCAGAAA     (SEQ ID NO: 38)
 92:  TAAGTATATCCTATGGCTATcag*tgatctgaAATTTAGGATAAAGCAGAAA    (SEQ ID NO: 39)
 95:  TAAGTATATCCTATGGCTATcagctgatATctgaAATTTAGGATAAAGCAGAA   (SEQ ID NO: 40)
 99:  TAAGTATATCCTATGGCT***********gaAATTTAGGATAAAGCAGAAA     (SEQ ID NO: 41)
101:  TAAGTATATCCTATGGCTATcCTA*****tgaAATTTAGGATAAAGCAGAAA    (SEQ ID NO: 42)
104:  TAAGTATATCCTATGGCTATcagct*****gaAATTTAGGATAAAGCAGAAA    (SEQ ID NO: 43)
106:  TAAGTATATCCTATGGCTATcag**gatctgaAATTTAGGATAAAGCAGAAA    (SEQ ID NO: 44)
111:  TAAGTATATCCTATGGCTATcCCc**atctgaAATTTAGGATAAAGCAGAAA    (SEQ ID NO: 45)
113:  TAAGTATATCCTATGGCTATcagctga*ctgaAATTTAGGATAAAGCAGAAA    (SEQ ID NO: 46)
122:  TAAGTATATCCTATGGCTATcagctgatTctgaAATTTAGGATAAAGCAGAAA   (SEQ ID NO: 47)
134:  TAAGTATATCCTATGGCTATcagc****ctgaAATTTAGGATAAAGCAGAAA    (SEQ ID NO: 48)
144:  TAAGTATATCCTATGGCTATcagct*atctgaAATTTAGGATAAAGCAGAAA    (SEQ ID NO: 49)
151:  TAAGTATATCCTATGGCTATcagctgatTctgaAATTTAGGATAAAGCAGAAA   (SEQ ID NO: 50)
154:  TAAGTATATCCTATGGCTATcagct*atctgaAATTTAGGATAAAGCAGAAA    (SEQ ID NO: 51)
156:  TAAGTATATCCTATGGCTATcagctgaAtctgaAATTTAGGATAAAGCAGAAA   (SEQ ID NO: 52)
161:  TAAGTATATCCTATGGCTATcagc****************ATAAAGCAGAAA    (SEQ ID NO: 53)
166:  TAAGTATATCCTATGGCTATcCT********aAATTTAGGATAAAGCAGAAA    (SEQ ID NO: 54)
171:  TAAGTATATCCTATGGCTATcagctg*tctgaAATTTAGGATAAAGCAGAAA    (SEQ ID NO: 55)
172:  TAAGTATATCCTATGGCTATcaAA*gatctgaAATTTAGGATAAAGCAGAAA    (SEQ ID NO: 56)
176:  TAAGTATATCCTATGGCTATca**tgatctgaAATTTAGGATAAAGCAGAAA    (SEQ ID NO: 57)
```

FIG.6

```
  W       ATTTTAATACTGGTgaacttggccatGACCATCTGGATTCTCAAA        (SEQ ID NO: 59)

6:  TGATGATTTTAATACTGGTgaa********tGACCATCTGGATTCTCAAA        (SEQ ID NO: 60)
  7:  TGATGATTTTAATACTGGTgaa*ttggccatGACCATCTGGATTCTCAAA        (SEQ ID NO: 61)
 20:  TGATGATTTTAATACTGGTga***********CCATCTGGATTCTCAAA         (SEQ ID NO: 62)
 21:  TGATGATTTTAATACTGGTgaa****gccatGACCATCTGGATTCTCAAA        (SEQ ID NO: 63)
 26:  TGATGATTTTAATACTGGTg****tggccatGACCATCTGGATTCTCAAA        (SEQ ID NO: 64)
 28:  TGATGATTTTAATACTGGTgaacttTTggccatGACCATCTGGATTCTCAAA      (SEQ ID NO: 65)
 31:  TGATGATTTTAATACTGGTgacttggTTGGccatGACCATCTGGATTCTCAAA     (SEQ ID NO: 66)
 34:  TGATGATTTTAATACTGGTgaact**gccatGACCATCTGGATTCTCAAA        (SEQ ID NO: 67)
 37:  TGATGATTTTAATACTG**************ACCATCTGGATTCTCAAA         (SEQ ID NO: 68)
 38:  TGATGATTTTAATACTGGTga***tggTcatGGCCATCTGGATTCTCAAA        (SEQ ID NO: 69)
 41:  TGATGATTTTAATACTGGTgaacttgg***GACCATCTGGATTCTCAAA         (SEQ ID NO: 70)
 43:  TGATGATTTTAATACTGGTgaac*****catGACCATCTGGATTCTCAAA        (SEQ ID NO: 71)
 46:  TGATGATTTTAATACTGGTgaac*****catGACCATCTGGATTCTCAAA        (SEQ ID NO: 72)
 48:  TGATGATTTTAATACTGGTgaacttTggccatGACCATCTGGATTCTCAAA       (SEQ ID NO: 73)
 49:  TGATGATTTTAATACTGGTgaa********tGACCATCTGGATTCTCAAA        (SEQ ID NO: 74)
 52:  TGATGATTTTAATAC************ccatGACCATCTGGATTCTCAAA        (SEQ ID NO: 75)
 55:  TGATGATTTTAATACTGGTgaa**tggccatGACCATCTGGATTCTCAAA        (SEQ ID NO: 76)
 66:  TGATGATTTTAATACTGG********ccatGACCATCTGGATTCTCAAA         (SEQ ID NO: 77)
 72:  TGATGATTTTAATACTGGTga***********CCATCTGGATTCTCAAA         (SEQ ID NO: 78)
 78:  TGATGATTTTAATACTGGTgattccatGACCATCTGGATTCTCAAA        (SEQ ID NO: 79)
 80:  TGATGATTTTAATACTGGTgaa**tggccatGACCATCTGGATTCTCAAA        (SEQ ID NO: 80)
 87:  TGATGATTTTAATACTGGTgaacttg*ccatGACCATCTGGATTCTCAAA        (SEQ ID NO: 81)
 91:  TGATGATTTTAATACTGGTgaacttggccatGACCATCTGGATTCTCAAA        (SEQ ID NO: 82)
 94:  TGATGATTTTAATACTGGTgaactt*****tGACCATCTGGATTCTCAAA        (SEQ ID NO: 83)
 97:  TGATGATTTTAATACTGGTga***tggTcatGACCATCTGGATTCTCAAA        (SEQ ID NO: 84)
100:  TGATGATTTTAAT******************GACCATCTGGATTCTCAAA        (SEQ ID NO: 85)
110:  TGATGATTTTAATACTGGTgaaTtAATACtggccatGACCATCTGGATTCTCAAA   (SEQ ID NO: 86)
113:  TGATGATTTTAATACTGGTga***tggccatGACCATCTGGATTCTCAAA        (SEQ ID NO: 87)
115:  TGATGATTTTAATACTGG********ccatGACCATCTGGATTCTCAAA         (SEQ ID NO: 88)
117:  TGATGATTTTAATACTGGTgaac**ggccatGACCATCTGGATTCTCAAA        (SEQ ID NO: 89)
118:  TGATGATTTTAATACTGGTga***********CCATCTGGATTCTCAAA         (SEQ ID NO: 90)
119:  TGATGATTTTAATACTGGTgaa********************TTCTCAAA        (SEQ ID NO: 91)
124:  TGATGATTTTAATACTGG*********************ATTCTCAAA          (SEQ ID NO: 92)
127:  TGATGATTTTAATACTGGTga******ccatGACCATCTGGATTCTCAAA        (SEQ ID NO: 93)
128:  TGATGATTTTAATACTGGTgaacttggccatGACCATCTGGATTCTCAAA        (SEQ ID NO: 94)
136:  TGATGATTTTAATACTGGTgaac**********CATCTGGATTCTCAAA         (SEQ ID NO: 95)
140:  TGATGATTTTAATACTGGTgaactt*gccatGACCATCTGGATTCTCAAA        (SEQ ID NO: 96)
144:  TGATGATTTTAATACTGGTgaactt******ACCATCTGGATTCTCAAA         (SEQ ID NO: 97)
161:  TGATGATTTTAATACTGGTgaacTTGGttggccatGACCATCTGGATTCTCAAA    (SEQ ID NO: 98)
164:  TGATGATTTTAATACTGGTgaa***ggccatGACCATCTGGATTCTCAAA        (SEQ ID NO: 99)
166:  TGATGATTTTAATACTGGTgaac**ggccatGACCATCTGGATTCTCAAA        (SEQ ID NO: 100)
167:  TGATGATTTTAATACTGGTgaac**ggccatGACCATCTGGATTCTCAAA        (SEQ ID NO: 101)
169:  TGATGATTTTAATACTGGTgaacttgCTG*******CCATCTGGATTCTCAAA     (SEQ ID NO: 102)
172:  TGATGATTTTAATACTGGTg*******ccatGACCATCTGGATTCTCAAA        (SEQ ID NO: 103)
172:  TGATGATTTTAATACTGGTg***********ACCATCTGGATTCTCAAA         (SEQ ID NO: 104)
174:  TGATGATTTTAATACTGGTga***********CCATCTGGATTCTCAAA         (SEQ ID NO: 105)
176:  TGATGATTTTAATACTGGTgaac**********CCATCTGGATTCTCAAA        (SEQ ID NO: 106)
177:  TGATGATTTTAATACTGGT*a***tggccatGACCATCTGGATTCTCAAA        (SEQ ID NO: 107)
```

DISEASE MODEL PIG EXHIBITING STABLE PHENOTYPE, AND PRODUCTION METHOD THEREOF

TECHNICAL FIELD

The present invention relates to disease model pigs exhibiting stable phenotypes and production methods thereof. The present invention also relates to chimeric pigs for producing disease model pigs exhibiting stable phenotypes, genital glands thereof, and germ cells thereof.

BACKGROUND ART

Genetically modified animals of large animals such as pigs can be produced by a somatic cell cloning technique from mammalian cells in which the function of a particular gene is modified using a gene disruption technique such as a genome editing technique or the like (Non-Patent Literature 1 to 4).

However, a phenotype derived from the responsible gene of the disease may not be necessarily obtained stably in many cases. This makes the production of genetically modified animals by somatic cell cloning techniques much less attractive.

CITATION LIST

Non Patent Literature

Non Patent Literature 1
 Nagashima H. et al., Biology of Reproduction 70: 702-707, 2004
Non Patent Literature 2
 Matsunari H. et al., Cloning and Stem Cells, 10: 313-323, 2008
Non Patent Literature 3
 Umeyama K. et al, Transgenic Res., 18: 697-706, 2009
Non Patent Literature 4
 Umeyama K. et al, Journal of Reproduction and Development, 59: 599-603, 2013

SUMMARY OF INVENTION

Technical Problem

The present invention provides disease model pigs exhibiting stable phenotypes and production methods thereof. The present invention also provides chimeric pigs for producing disease model pigs exhibiting stable phenotypes, genital glands thereof, and germ cells thereof.

Solution to Problem

The present inventors have found that genetically modified pigs produced by the somatic cell cloning have a problem that their phenotypes are unstable and removing the epigenetic effect of somatic cells can eliminate this problem and yield genetically modified pigs having stable phenotypes. The present inventors have found that a hyperammonemia model pig could be produced by, moreover, destructing the function of the ornithine transcarbamylase gene. The present inventors have also found that dilated cardiomyopathy model pigs can be produced by disturbing the function of the δ-sarcoglycan gene. Moreover, the present inventors have found a method for reducing the epigenetic effect on these model pigs. Furthermore, the present inventors have found that the production of chimeric embryos is useful to produce disease model pigs exhibiting stable phenotypes even if the genetic modification to be achieved is fatal. The present invention is based on these findings and inventions.

Accordingly, the present invention provides the following inventions.

(1) A method for producing a genetically modified disease model pig, comprising:
 (a) transplanting a nucleus of a genetically modified cell into cytoplasm of an egg;
 (b) developing an obtained clonal embryo in a womb of a female pig to obtain an offspring; and
 (c) mating the obtained offspring or having the offspring undergo sexual reproduction to further obtain the genetically modified offspring as a disease model pig.

(2) The method according to (1) above, wherein the disease model pig is a model pig of a disease selected from the group consisting of diabetes, hyperammonemia, and dilated cardiomyopathy.

(3) The method according to (2) above, wherein the disease model pig is diabetes model animal and the cell used in (a) above is a cell genetically modified by introducing a dominant negative mutant of HNF-1α.

(4) The method according to (2) above, wherein the disease model pig is a dilated cardiomyopathy model pig.

(5) The method according to any one of (2) to (4) above, wherein the disease phenotype is a dominant trait.

(6) The disease model pig obtained by a method according to any one of (1) to (5) above.

(7) A method for producing a fatal genetic disease model pig, comprising:
 (i) transplanting a nucleus of a genetically modified cell into cytoplasm of an egg;
 (ii) making a chimera of a clonal embryo obtained by the nuclear transplantation and an embryo of a pig not developing the genetic disease and developing the chimera in a womb of a female pig to obtain an offspring;
 (iii) mating the obtained offspring or having a germ cell of the obtained offspring undergo sexual reproduction to obtain a female offspring having the genetic modification; and
 (iv) mating the obtained female offspring or having the offspring undergo sexual reproduction with a male pig to obtain a fatal genetic disease model pig.

(8) The method according to (7) above, wherein the fatal genetic disease is hyperammonemia.

(9) The method according to claim 7, wherein the fatal genetic disease is dilated cardiomyopathy.

(10) The fatal genetic disease model pig obtained by a method according to any one of (7) to (9) above.

(11) A hyperammonemia model pig in which the gene function of the ornithine transcarbamylase gene is disrupted.

(12) A hyperammonemia model pig having a deletion of a part of the second exon in the ornithine transcarbamylase gene leading to a nonsense mutation.

(13) A genetically modified pig comprising a somatic chimera of cells having a dysfunctional ornithine transcarbamylase gene and cells having a wildtype ornithine transcarbamylase gene.

(14) A female pig obtained by sexual reproduction of a pig according to (13) above, wherein the pig has a heterozygous dysfunctional ornithine transcarbamylase gene.

(15) A male pig obtained by sexual reproduction of a pig according to (14) above, wherein the pig is a hyperammonemia model.

(16) A dilated cardiomyopathy model pig in which the gene function of the δ-sarcoglycan gene is disrupted.
(17) A dilated cardiomyopathy model pig having a deletion of a part of the second exon of the δ-sarcoglycan gene leading to a nonsense mutation.
(18) A genetically modified pig comprising a somatic chimera of cells having a dysfunctional δ-sarcoglycan gene and cells having a wildtype δ-sarcoglycan gene.
(19) A female pig obtained by sexual reproduction of a pig according to (18) above, wherein the pig has a heterozygous dysfunctional δ-sarcoglycan gene.
(20) A male pig obtained by sexual reproduction of a female pig according to (19) above, wherein the pig has a homozygous dysfunctional δ-sarcoglycan gene and is a dilated cardiomyopathy model.
(21) A genital gland or a germ cell obtained by a method comprising:
(i) transplanting a nucleus of a genetically modified cell into cytoplasm of an egg;
(ii) making a chimera of a clonal embryo obtained by the nuclear transplantation and an embryo of a pig not developing the genetic disease and developing the chimera in a womb of a female pig to obtain an offspring; and
(iii-a) growing an obtained offspring to obtain a genital gland or a germ cell.
(22) The genital gland or germ cell according to (21) above, wherein the genetically modified cell is a cell in which the gene function of the ornithine transcarbamylase gene is disrupted or a cell in which the gene function of the δ-sarcoglycan gene is disrupted.

BRIEF DESCRIPTION OF DRAWINGS

FIG. 4 illustrates the sequences of the modified OCT genes (SEQ ID NOs: 18-57).
FIG. 6 illustrates the sequences of the modified SGCD genes (SEQ ID NOs: 59-107).

DESCRIPTION OF EMBODIMENTS

Figure 1:
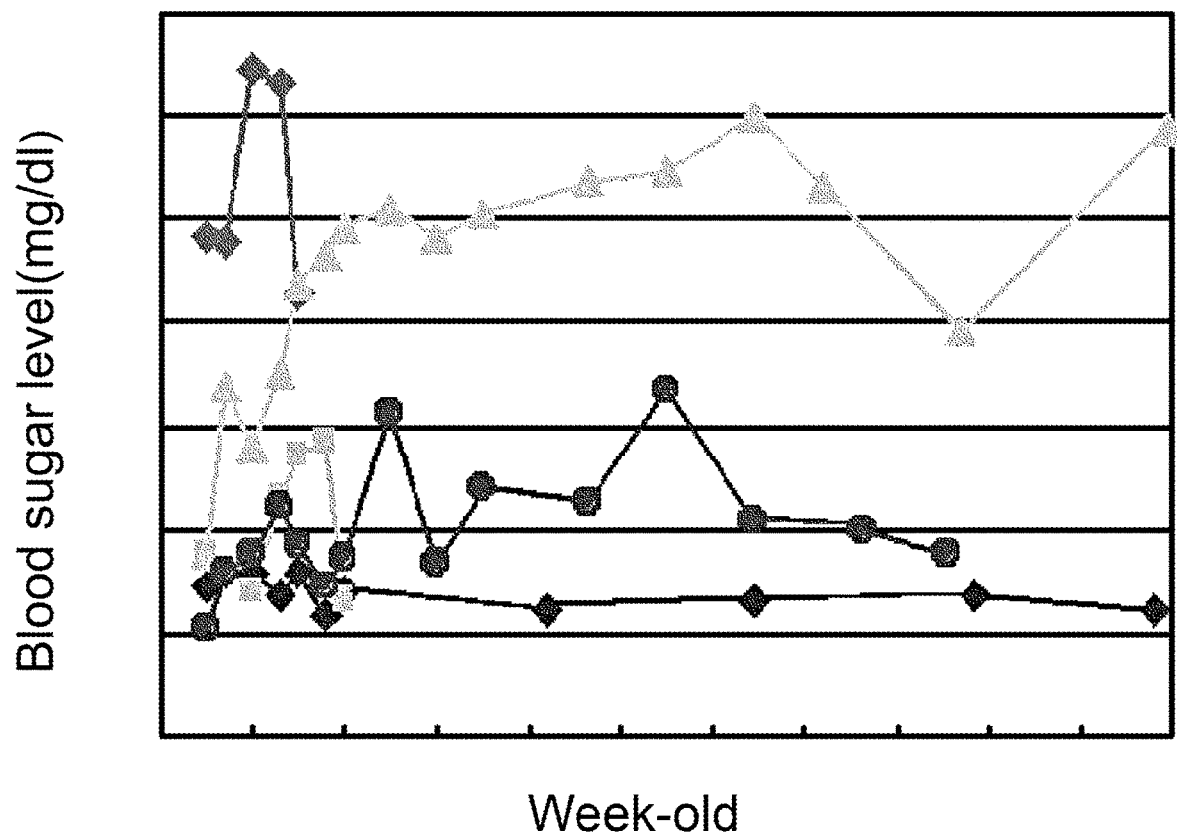
FIG. 1 is a graph illustrating the change over time of blood glucose level in 5 pigs obtained by somatic cell cloning using nuclei of genetically modified cells.

As used herein, "genetically modified" means that a gene is modified by a genetic engineering technique to lose at least a part or all of its function or to have an excessively enhanced function. The genetic modification includes that by introduction of a gene and that by modification of a genomic gene. The genetic modification of large animals such as pigs can be performed by obtaining genetically modified offspring as a genetically modified animal by somatic cell cloning of nucleus of a genetically modified cell.

As used herein, the "disease model pig" means a pig that exhibits symptoms of a specific disease by genetic modification. Examples of such a disease include, but are not limited to, diabetes, hyperammonemia, and dilated cardiomyopathy. In a certain embodiment, the disease may be hereditary.

As used herein, the "somatic cell cloning" refers to a technique involving introducing a somatic nucleus into an unfertilized egg in which the nucleus has been inactivated or eliminated to obtain an individual having the genome same as the somatic cell. Somatic cell cloning is known to be used in the production of genetically modified animals such as transgenic animals and knockout animals in large animals including pig. The somatic cell cloning can be generally performed by transplanting a nucleus removed from a somatic cell differentiated into skin, a tissue, or an organ into an egg cell (egg cell cytoplasm) derived from another individual in which the nucleus is removed to produce a clonal embryo and transplanting the egg cell into the uterus of a surrogate parent that is a different individual that have undergone estrous synchronization.

As used herein, "mating" means mating a male and a female. As used herein, "subjecting to sexual reproduction" means bringing an ovum in contact with sperms in vivo or in vitro to fertilize the ovum and developing the ovum in a uterus to obtain an offspring.

As used herein, a "dominant trait" means that heterozygote with a mutant gene and a wild type gene expresses the trait based on the mutant gene as a phenotype. As used herein, a "recessive trait" means that heterozygote with a mutant gene and a wild type gene does not express the trait based on the mutant gene as a phenotype.

As used herein, "ornithine carbamoyltransferase" is synonymous with "ornithine transcarbamylase" and "OTC". As used herein, δ-sarcoglycan" is synonymous with "SGCD".

The present inventors found in production of model pigs of type 3 maturity-onset diabetes of the young that the first generation offspring obtained by somatic cell cloning have unstable phenotypes. The present inventors also found that when further offspring (second generation) were obtained by sexual reproduction from the first generation offspring, the second generation offspring have stable diabetic phenotypes. This suggests that an epigenetic state that is characteristic of embryos, fetuses, or individuals generated by somatic cell cloning influences phenotypes of the first generation and that this epigenetic state disappears in the second generation and phenotypes based on the genetic mutation appears apparently.

Thus, according to the present invention, a method for producing a genetically modified disease model pig, comprising:
(a) transplanting a nucleus of a genetically modified cell into cytoplasm of an egg;
(b) developing an obtained clonal embryo in a womb of a female pig to obtain an offspring; and
(c) mating the obtained offspring or subjecting the offspring to sexual reproduction to further obtain the genetically modified offspring as a disease model pig;
is provided.

The method according to the present invention is described step by step below.

(a) Transplanting a Nucleus of a Genetically Modified Cell into Cytoplasm of an Egg Cells can be modified by well-known genetic modification techniques.

Examples of the methods for genetically modifying the genome of cells include methods involving editing the genome by a genome editing technique such as TALEN as well as methods involving modifying a gene in the genome such as methods involving disrupting a gene and methods involving introducing an exogenous gene by homologous recombination and methods involving introducing an exogenous gene with a virus vector. The modification of cells may be conducted by a method involving introducing DNA, RNA or protein into a cell without modifying the genome.

TALEN is a hybrid enzyme in which a DNA binding domain consisting of amino acid 33 to 35 highly conserved in the TALE (Transcription Activator-Like Effector) protein derived from *Xanthomonas*, a plant pathogenic bacterium is fused with a nuclease domain of the FokI protein and well-known as a tool of genome editing. Accordingly, the cells may be modified by introduction of an exogenous gene to be transgenic or by disruption of a part or all of the function of a gene to be a knockout.

In (a), the genetic modification is one that causes a genetic disease. A person skilled in the art can select as appropriate the gene to be introduced or disrupted to cause the genetic disease according to the disease model to be produced.

To produce a diabetes model pig, a gene, for example, but not particularly limited to, a dominant negative mutant HNF-1α, may be introduced. Examples of the dominant negative mutant HNF-1α that can be used include human or pig dominant negative mutant HNF-1α and HNF-1αP291fsinsC. HNF-1αP291fsinsC has been discovered as a causative gene of maturity-onset diabetes of the young, has the nucleotide sequence of SEQ ID NO: 3, and encodes a protein having the amino acid sequence of SEQ ID NO: 4. Human HNF-1α is a protein having 631 amino acids but HNF-1αP291fsinsC has a mutation that inserts one cytosine nucleotide in the 8 consecutive cytosine nucleotides from the nucleotide 1091 to the nucleotide 1098 in human HNF-1α to change the 316th codon into a stop codon as shown in SEQ ID NO: 3 and it is produced as a truncated protein, which is shorter than the original protein.
Overexpression of this dominant negative mutant inhibits the normal function of HNF-1α and exhibits the diabetic phenotype.

To produce a hyperammonemia model, a gene, for example, but not particularly limited to, the ornithine transcarbamylase (OTC) gene, may be disrupted. The OTC gene locates on the X chromosome, a sex chromosome, and is considered to consist of 10 exons. The coding region of the OTC gene in pig is set forth in nucleotide 42 to nucleotide 1106 in SEQ ID NO: 5 and the amino acid sequence is set forth in SEQ ID NO: 6. The disruption of the OTC gene in a male results in development of hyperammonemia and a heterozygous female of a wild type and a mutant may be a career or develop hyperammonemia with additional factors. The disruption of the OTC gene can be performed by, for example, by modifying the gene to generate a nonsense codon. For example, the OTC gene may be disrupted by modifying any one of the 1st to the 3rd exons, preferably the 2nd to generate a nonsense codon. Such a nonsense codon can be generated, for example, using a genetic modification technique such as TALEN and site-directed mutagenesis. TALEN has been reported to have a low off target effect, cleavage of unintended DNA, in comparison with other mutagenesis techniques (methods involving zinc finger nuclease (ZEN) or CRISPR/Cas9) (Ain et al., J Control Release (2015)). An example of the second exon sequence having a generated nonsense codon in pig is set forth in SEQ ID NO: 8, in which a part of the 2nd exon, nucleotide 109 to nucleotide 113 of the nucleotide sequence of SEQ ID NO: is deleted to change the 64th codon in the nucleotide sequence of SEQ ID NO: 5 into a nonsense codon, and the resultant amino acid sequence is set forth in SEQ ID NO: 10.

To produce a dilated cardiomyopathy model pig, a gene, for example, but not particularly limited to, δ-sarcoglycan (SGCD) gene can be modified. The SGCD gene locates on chromosome 16 and is considered to consist of 8 exons. The coding region of the SGCD gene in pig is set forth in 77-946 of SEQ ID NO: 11 and the amino acid sequence is set forth in SEQ ID NO: 13. The disruption of the SGCD gene can be performed by, for example, by modifying the gene to generate a nonsense codon. For example, the SGCD gene may be disrupted by modifying any one of the 1st to the 3rd exons, preferably the 2nd to generate a nonsense codon. Such a nonsense codon can be generated, for example, using a genetic modification technique such as TALEN and site-directed mutagenesis. An example of the second exon sequence having a generated nonsense codon in pig is set forth in SEQ ID NO: 13, in which a part of the 2nd exon, nucleotide 208 to nucleotide 211 of the nucleotide sequence of SEQ ID NO: 11, is deleted to change the 50th codon in the amino acid sequence of SEQ ID NO: 11 into a nonsense codon, and the resultant amino acid sequence is set forth in SEQ ID NO: 14. Alternatively, 1859 nucleotides upstream of nucleotide 147 in the second exon of the SGCD gene set forth in SEQ ID NO: 15 may be deleted to generate the sequence set forth in SEQ ID NO: 16 and thereby delete the region including the start codon.

Moreover, the genetic modification may be performed using, besides TALEN, other well-known techniques such as homologous recombination or site directed mutagenesis.

A genetically modified cell so obtained may be selected by a technique, for example, but not particularly limited to, sequencing of the modified gene or expression of a selection marker. It is desirable to clone the selected cell.

Subsequently, the nucleus of the genetically modified cell may be used in somatic cell cloning.

(b) Developing an Obtained Clonal Embryo in a Womb of a Female Pig to Obtain an Offspring The obtained clonal embryo can be developed in the womb of a female pig and offspring consisting of genetically modified cells (i.e., genetically modified pig) can be thereby obtained. The pregnancy in the womb may be established by conducting the estrus synchronization of the female pig before introducing the clonal embryo into its uterus and the offspring can be obtained by developing the clonal embryo. The pigs obtained in (b) may be referred to as the first generation pigs.

(c) Mating the Obtained Offspring or Subjecting the Offspring to Sexual Reproduction to Further Obtain the Genetically Modified Offspring as a Disease Model Pig If the offspring can mature sexually, then genetically modified next-generation pigs (which may be also referred to as the "second generation pigs") can be obtained by mating the offspring after the sexual maturation or subjecting the offspring to the sexual reproduction. If the offspring die before the sexual maturation, the genetically modified next-generation pigs can be obtained by methods such as artificial insemination or in vitro fertilization after obtaining germ cells (sperms, ova, and precursor cells thereof) or genital glands by a well-known method.

The sperms may be collected, for example, from a testis or obtained by inducing sperms having fertility from a testicular tissue. Methods for inducing sperms having fertility from a testicular tissue are not particularly limited, but, for example, it is known that sperms having fertility can be obtained by transplanting a testicular tissue under skin of an immunodeficient mouse.

If the modified gene is of a dominant trait (for example, when a dominant negative mutant is introduced), the offspring thus obtained in (c) develop the disease and become the disease model pigs. On the other hand, if the modified gene is of recessive trait (including the case that the gene locates on a sex chromosome and the individual is female), the individual does not develop the disease, but becomes a career of the mutant gene. If the genetically modified gene is recessive and locates on a sex chromosome, male pigs develop the disease and become the disease model pigs and female pigs do not develop the disease and become careers of the modified gene. Careers of the modified gene may be mated to obtain the disease model pigs. The relations described above are illustrated in Table 1.

TABLE 1

Relation between character of modified gene and phenotype of offspring

| Dominant/Recessive | X chromosome/Autosome | Male phenotype | Female phenotype |
| --- | --- | --- | --- |
| Dominant | Both | Disease development | Disease development |
| Recessive | X chromosome | Disease development | No development (Carrier) |
| Recessive | Autosome | No development (Carrier) | No development (Carrier) |

* Note
that a carrier may develop disease with another factor.

Accordingly, if the obtained offspring develops the disease, they are obtained as disease model pigs and if they are careers, the sexual reproduction between the offspring that are carriers can yield the offspring that develop the disease.

Examples of dominant genetic mutants include disease model pigs into which a dominant negative mutation is introduced and disease model pigs having a genetic mutation exhibiting a dominant trait. These offspring having such a dominant genetic mutation become model pigs that develop a disease. Examples of the genetic mutation exhibiting such a dominant trait include dominant negative mutants of HNF-1α and transgenic animals in which this mutant is introduced become model pigs that develop diabetes. Moreover, disease model pigs that have lost at least a part of the functions of a gene locating on X chromosome also produce offspring that become model pigs that develop a disease. Examples of such a gene that locates on X chromosome and causes a disease when at least part of the functions thereof is lost include the ornithine transcarbamylase (OTC) gene and elimination of at least part of the functions produces model pigs that develop hyperammonemia.

If the offspring are carriers of a recessive genetic mutation, (c) above may be (c) mating the obtained offspring or subjecting the offspring to sexual reproduction to obtain further genetically modified offspring as offspring that is heterozygous of the genetic mutation (that is to say, carriers of the recessive genetic mutation);

and subsequently, (d) subjecting the carriers of the recessive genetic mutation to sexual reproduction to obtain offspring having homozygous genetic mutation as a disease model pig can be further conducted.

Moreover, if the offspring are carriers of a genetic mutation on X chromosome, (c) above may be (c) mating the obtained offspring or subjecting the offspring to sexual reproduction to obtain further genetically modified offspring as offspring that is heterozygous of the genetic mutation (that is to say, carriers of the recessive genetic mutation);

and subsequently, (d) subjecting a female carrier having the genetic mutation on X chromosome to sexual reproduction to obtain a male offspring as a disease model pig.

can be further conducted.

Examples of a gene that locates on an autosome and causes a disease when at least a part or all of the functions thereof is eliminated include the δ-sarcoglycan (SGCD) gene and homozygous knock-outs become pigs that develop dilated cardiomyopathy.

In relation with this, if the pigs obtained by somatic cell cloning die before the sexual maturation due to the effect of the disease, a testicular tissue is collected from live pigs before the sexual maturation and sperms obtained from the tissue may be used for mating. Methods for obtaining sperms from a testicular tissue are well-known and not particularly limited, but, for example, it is known that sperms having fertility are obtained by transplanting a testicular tissue under skin of an immunodeficient mouse. In the present invention, sperms having fertility can be obtained from a testicular tissue by such a method. Accordingly, as used herein, having "sexual reproduction" is not particularly limited as long as an offspring is obtained in a way of sexual reproduction and encompasses various methods for obtaining an offspring from a male and a female.

In (c) above, female offspring can be obtained as carriers among heterozygous offspring of the genetic mutation (that is to say, carriers of the recessive genetic mutation). The female carriers and the disease model pigs obtained as offspring thereof in (d) above can become a model that closely reproduces phenotypes of human patients born from mothers who are human carriers. In the present invention, the carriers and/or disease model pigs obtained as offspring thereof in (d) above are provided.

Moreover, in (c) above, female pigs having a genetic mutation on X chromosome can be obtained as carriers. The female carriers and the disease model pigs obtained as offspring thereof in (d) above can become a model that closely reproduces phenotypes of human male patients born from mothers who are human carriers. In the present invention, the carriers and/or male disease model pigs obtained as offspring thereof in (d) above are provided.

Moreover, even if pigs obtained by somatic cell cloning die before obtaining a testis or ovary due to the effect of the disease, it is possible to form chimeras of an embryo of a pig obtained by somatic cell cloning and an embryo of a pig that does not develop the genetic disease, transplant the chimeras in surrogate mothers that have undergone estrus synchronization, produce chimeric individuals, sexually mature the individuals after reducing the effect of the disease, or collect a genital gland (for example, a testis and an ovary) or germ cells (sperms, ova, and precursor cells thereof) and mature them as needed, and subject them to sexual reproduction. In this way, it is possible to sexually mature embryos or collect, and mature as needed, genital glands and have them undergo sexual reproduction to obtain disease model pigs or carrier pigs, as long as the embryos are developed and grown in a chimeric state. The disease model pigs or carrier pigs thus obtained are considered to be free of the epigenetic effect of somatic cell cloning.

Thus, according to the present invention, a method for producing a genetic disease model pig, comprising:

(i) transplanting a nucleus of a genetically modified cell into cytoplasm of an egg;

(ii) mixing a clonal embryo obtained by the nuclear transplantation and an embryo of a pig not developing the genetic disease to make a chimera and developing the chimera in a womb of a female pig to obtain an offspring; and (iii) mating the obtained offspring or subjecting a germ cell of the obtained offspring to sexual reproduction to obtain an offspring having the genetic modification; is provided.

The genetic disease may be a fatal disease.

Examples of the fatal disease include hyperammonemia and dilated cardiomyopathy.

(i) to (iv) above are described step by step below.
(i) Transplanting a Nucleus of a Genetically Modified Cell into Cytoplasm of an Egg (i) is the same as (a) described above. Therefore, the description of (a) is to be referred for (i) and the description of (i) is omitted here.
(ii) Mixing a Clonal Embryo Obtained by the Nuclear Transplantation and an Embryo of a Pig not Developing the Genetic Disease to Make a Chimera and Developing the Chimera in a Womb of a Female Pig to Obtain an Offspring An embryo obtained by the nuclear transplantation using a somatic cell (somatic cell cloning) can be mixed with an embryo of a pig that does not develop the genetic disease to make a chimera and an offspring can be obtained by developing the chimera in the womb of a female pig. For mixing embryos, when using an embryo in early cleavage (the 1-cell stage to the morula stage), its blastomeres may be mixed with another embryo and when using an embryo in the blastocyst stage, its internal cell mass may be mixed with another embryo. The embryo of the pig that does not develop the genetic disease may be, in a certain embodiment, a clonal embryo obtained by somatic cell cloning from labelled cells. In this specific aspect, the label is, for example, but not particularly limited to, a label with a fluorescent protein such as Kusabira Orange and green fluorescent protein (GFP). The chimeric embryo may be, for example, transplanted into a surrogate mother that have undergone estrus synchronization and developed into a chimeric individual to obtain an offspring. In the present invention, a chimeric individual thus obtained is provided.

Techniques to make an embryo chimeric is well-known and available for the present invention. For example, Step (x): a nuclear transplanted embryo (clonal embryo) having a fatal genetic mutation and a nuclear transplanted embryo or a normal embryo that does not have the genetic mutation are produced. Either of the nuclear transplanted embryos may be one that has once cryopreserved.

Step (y): to one embryo in early cleavage (the 1-cell stage to the morula stage), blastomeres obtained from the other embryo in the same developmental stage are injected, which allows blastomeres of the both aggregated in the zona pellucida to generate a chimera. In step (y), an embryo in the blastocyst stage may be also used. When an embryo in the blastocyst stage is used, to one blastocyst, the whole or a part of separated inner cell mass from the other embryo is injected to generate a chimera.

Step (z): after observing the progress in the chimeric state in vitro culture for from several hours to several days or so, the chimeric embryo is transplanted in the oviduct or the uterus in a surrogate mother and developed.

Since the offspring are chimeric individuals having cells from a pig that develops the genetic disease and cells from a pig that does not develop the genetic disease, the symptoms of the genetic disease can be alleviated. This allows the chimeric individuals to grow till the sexual maturation or to the extent that a genital gland (for example, a testicular tissue, and an ovarian tissue) and germ cells (sperms, ova, and precursors thereof) are formed.

In a certain embodiment of the present invention, germ cells (sperms, ova, and precursor cells thereof) and genital glands (testes and ovaries) obtained from chimeric individuals obtained by step (ii) are provided. Such germ cells and genital glands have been difficult to obtain if the genetic modification is fatal. Such a genital gland is a chimera of cells from a clonal embryo having a modified gene and cells derived from a normal embryo. In a certain embodiment, the germ cells (sperms, ova, and precursor cells thereof) and genital glands (testes and ovaries) according to the present invention have a genetic modification that does not let the individual survive or makes the individual hard to survive.
(iii) Mating the Obtained Offspring or Subjecting a Germ Cell of the Obtained Offspring to Sexual Reproduction to Obtain an Offspring Having the Genetic Modification (iii) is the same as (c) described above. Therefore, the description of (c) is to be referred for (iii) and the description of (iii) is omitted here. If the offspring develops the disease, then the offspring is considered to be obtained as the disease model pig. On the other hand, if the offspring does not develop the disease, then the offspring is considered to be obtained as a carrier. The present invention provides also a carrier (for example, female or male carrier) having a genetic mutation. If the offspring obtained in (iii) is a carrier, then (iv) below may be further conducted.
(iv) Mating the Obtained Offspring or Subjecting the Offspring to Sexual Reproduction to Obtain a Disease Model Pig Having the Genetic Modification (iv) is the same as (d) above. Accordingly, it is possible to subject carriers of a recessive genetic mutation to sexual reproduction or subject a female carrier having the genetic mutation on X chromosome to sexual reproduction to obtain an offspring that is homozygous for the genetic mutation as a disease model pig.

In (iii) above, female offspring can be obtained as carriers among heterozygous offspring of the genetic mutation (that is to say, carriers of the recessive genetic mutation). The female carriers and the disease model pigs obtained as offspring thereof in (iv) above can become a model that closely reproduces phenotypes of human male patients born from mothers who are human carriers. In the present invention, female carriers and/or disease model pigs obtained as offspring thereof in (iv) above are provided.

Moreover, in (iv) above, female pigs having a genetic mutation on X chromosome can be obtained as carriers. The female carriers and the disease model male pigs obtained as offspring thereof in (iv) above can become a model that closely reproduces phenotypes of human male patients born from mothers who are human carriers. Female carriers and/or disease model pigs obtained as offspring thereof in (iv) above, wherein the model pigs have a genetic mutation on X chromosome, are provided.

In another aspect of the present invention, the present invention provides a genetically modified pig or a population of genetically modified pigs having a uniform phenotype, obtained by a method according to the present invention.

Specific Examples are described below for illustration. The present invention is however not limited to Examples, but identified by the scope of the invention stated in the claims.

EXAMPLES

Example 1: Production of Diabetes Model Pig and Analysis of Phenotype Thereof

In this Example, a process for producing diabetes model pigs was conducted based on the description in Umeyama K. et al., Transgenic Res. 18: 697-706 (2009) and phenotypes thereof were analyzed in detail.

First, diabetes model pigs were produced based on the description by Umeyama K. et al., (2009). Specifically, cDNA of a dominant negative mutant (HNF-1αP291fsinsC) of human HNF-1α known as a causative gene of type 3 maturity-onset diabetes of the young was operably linked to an enhancer of immediate early genes of human CMV and a pig insulin promoter and to downstream thereof, human HNF-1αP291fsinsC, a poly A addition signal, and a chicken β-globin insulator were linked to construct an expression unit and then a human mutant HNF-1α expression plasmid was obtained.

The human mutant HNF-1α expression unit was excised from the expression plasmid, the DNA was brought into contact with the surface of sperms, and this expression unit was introduced into an ovum matured in vitro by gene introduction by intracytoplasmic sperm injection. The ovum is returned to a pig, cells from the kidney, the lung, and the muscle in pig were obtained, and nuclei thereof were transplanted in egg cytoplasm (as for the details of the method, see Kurome K. et al., Transgenic Research 15: 229-240 (2006)).

Analysis of the obtained pigs revealed that pigs exhibiting the phenotype of diabetes were obtained. The results of analysis of plural obtained pigs are illustrated in FIG. 1.

FIG. 1 illustrates the blood glucose level in 5 pigs and its change. All individuals are clonal individuals derived from the same cell into which the human HNF-1αP291fsinsC gene is introduced. However, it was found that, as illustrated in FIG. 1, the change of the blood glucose level varies greatly among the obtained pigs and their life spans were also greatly different. Therefore, it was revealed that further improvement was required for this diabetes model.

Example 2: Production of Model Pig Exhibiting Stable Diabetic Phenotype

In this Example, the offspring obtained from diabetes model pigs obtained in Example 1 were analyzed.

Figure 2:
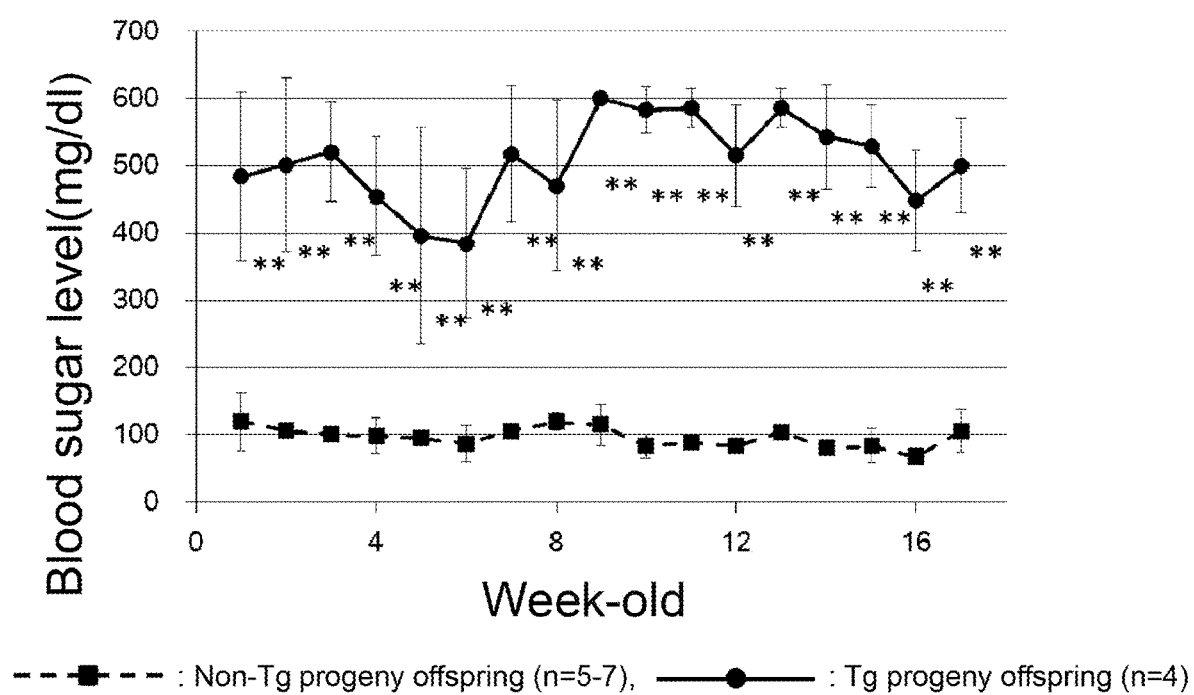
FIG. 2 is a graph illustrating the change over time of blood glucose level in next-generation descendants produced by subjecting pigs obtained by somatic cell cloning to sexual reproduction (mating). The Tg progeny offspring indicates next-generation descendants of genetically modified pigs obtained by somatic cell cloning and the non-Tg progeny offspring indicates pigs with no genetic modifications.

The diabetes model pigs obtained in Example 1 were sexually matured by insulin administration, sperms were collected, and artificial insemination was conducted. Embryos were transplanted into surrogate mothers that underwent estrus synchronization, the pregnancy was established, and offspring were obtained. The results of analysis on the diabetic phenotype of the obtained offspring were illustrated in FIG. 2. FIG. 2 illustrates the diabetic phenotype of a representative offspring among plural offspring.

It was revealed that, as illustrated in FIG. 2, the casual blood glucose level of the obtained offspring was stable over weeks and it was a good diabetes model.

Moreover, offspring of an individual that exhibited a different phenotype among the diabetes models obtained in Example 1 were similarly analyzed. It was revealed that these offspring were also stable over weeks and were good diabetes models (data not shown).

It is possible that the difference of the epigenetic state of cells used in nuclear transplantation may be involved in the difference of the phenotype between individuals. The reason why the phenotype was stable in these offspring is considered that the epigenetic state mentioned above was eliminated by the fertilization.

This Example revealed that it is possible to make the phenotype of animals (for example, disease models) obtained by nuclear transplantation more stable by obtaining offspring after nuclear transplantation.

The above results revealed that the epigenetic state of cells used in somatic cell cloning has a large effect on the phenotype of offspring obtained from embryos obtained by somatic cell cloning. It was revealed that this epigenetic effect can be eliminated by obtaining next-generation offspring.

Example 3 Production of Hyperammonemia Model Pig

In this Example, a process for producing hyperammonemia model pigs was conducted.

Figure 3:
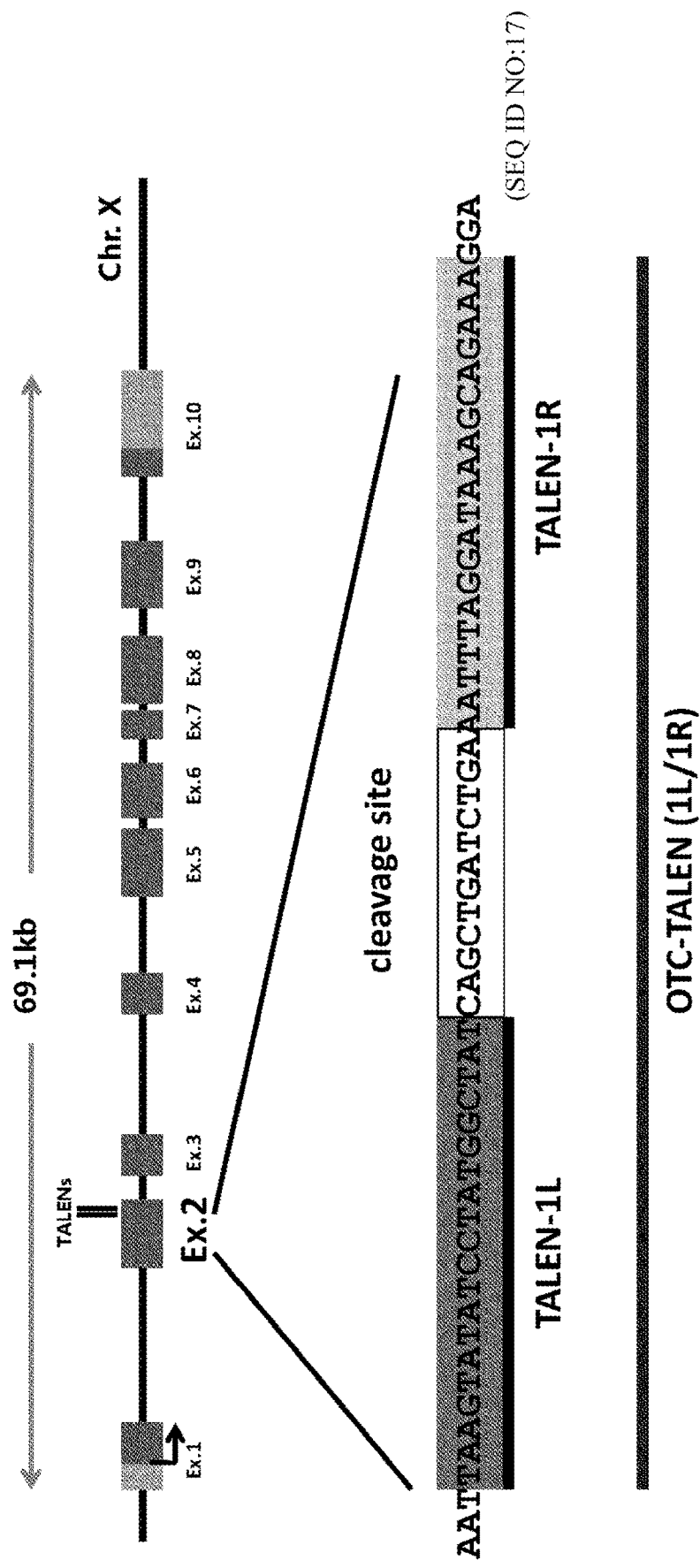
FIG. 3 is a drawing illustrating the structure of ornithine transcarbamylase (OTC) gene (SEQ ID NO: 17) on a sex chromosome (an X chromosome) of the pig and a modification technique of the OTC gene using the genome editing technique.

The gene disruption of ornithine transcarbamylase (OTC) was conducted as follows. As illustrated in FIG. 3, OTC locates on X chromosome and is considered to consist of 10 exons. OTC-TALEN that targets the second exon was constructed (FIG. 3).

The mRNA encoding TALEN was introduced into fetus fibroblasts of a male pig by electroporation. 176 clones obtained by limiting dilution of the cells were subsequently analyzed on the DNA sequence targeted by the TALEN and mutations were found in 43 clones (FIG. 4). Among the obtained clones, the clone No. 69 had a 5 nucleotide deletion in the second exon. In further experiments, this clone was used to produce hyperammonemia model pigs. It was considered that, in the clone No. 69, the 5 nucleotide deletion generated a stop codon and this caused disruption of the OTC gene function.

Somatic cell cloning was conducted by a method described in Matsunari et al., Cloning and Stem Cells, Vol. 10, No. 3, 313-323, 2008 using the nucleus of the No. 69 OCT gene disruptant clone, embryos obtained by the somatic cell cloning were transplanted into surrogate mothers that underwent estrus synchronization, and the pregnancy was established. OTC gene-knockout pigs were obtained from pregnant female pigs by natural childbirth and cesarean section.

Analysis of the obtained offspring revealed that these offspring developed hyperammonemia (Table 2). The general symptoms of the offspring were severer than symptoms estimated from symptoms (for example, convulsions) of usual OTC gene-deficient (OTCD) patients (Table 2). Analysis of plural offspring revealed that the phenotypes were greatly different among individuals (Table 2).

TABLE 2

|  | OCT KO clone | | WT |
|---|---|---|---|
| Individual No. | #1 | #2 | #3, #4 |
| Blood ammonia concentration (N-µg/dL) | >400* | >400* | 34, 68.5 |
| Symptom Convulsions | detected | detected | not-detected |
| Impaired consciousness | detected | detected | not-detected |

*Above the detection upper limit and not measurable

Next, an embryo (female) was produced by somatic cell cloning from a cell expressing humanized Kusabira Orange, a chimeric embryo was made with an embryo (male) obtained by somatic cell cloning using the nucleus of the No. 69 OCT gene disruptant clone, the embryo was transplanted into a surrogate mother that underwent estrus synchronization, and a chimeric individual was produced. The obtained chimeric individual was male.

This chimeric individual reaches sexual maturation and produced sperms having the OTC gene deficiency.

The obtained chimeric individual was mated with a wild-type female to yield the second generation offspring. Among the offspring, the female individuals had the OTC gene deficiency on one X chromosome and became an OTCD career or developed OTCD under the effect of another trigger.

As seen above, a chimeric individual evading from a fatal phenotype was obtained by producing a clonal embryo from a cell of an individual that was generated by somatic cell cloning and has a fatal OTC gene deficiency and making a chimeric embryo thereof with a normal embryo. By subjecting this chimeric individual to sexual reproduction, female pigs having a closely reproduced OTC gene deficiency were successfully produced.

The third generation individuals can be obtained by subjecting the female pigs having a closely reproduced OTC gene deficiency to mating or other sexual reproduction. Among the third generation individuals, male individuals having the OTC gene deficiency will be model animals that reproduce the phenotype of human male patients born from mothers who are carriers of the OTC gene deficiency.

Moreover, the obtained third generation individuals will be model animals that closely reproduce the pathology free of the epigenetic effect present in the first generation, that is to say, the phenotype of human male patients born from mothers who are carriers.

Example 4: Production of Dilated Cardiomyopathy Model Pig

In this Example, a process for producing dilated cardiomyopathy model pigs was conducted.

Figure 5:
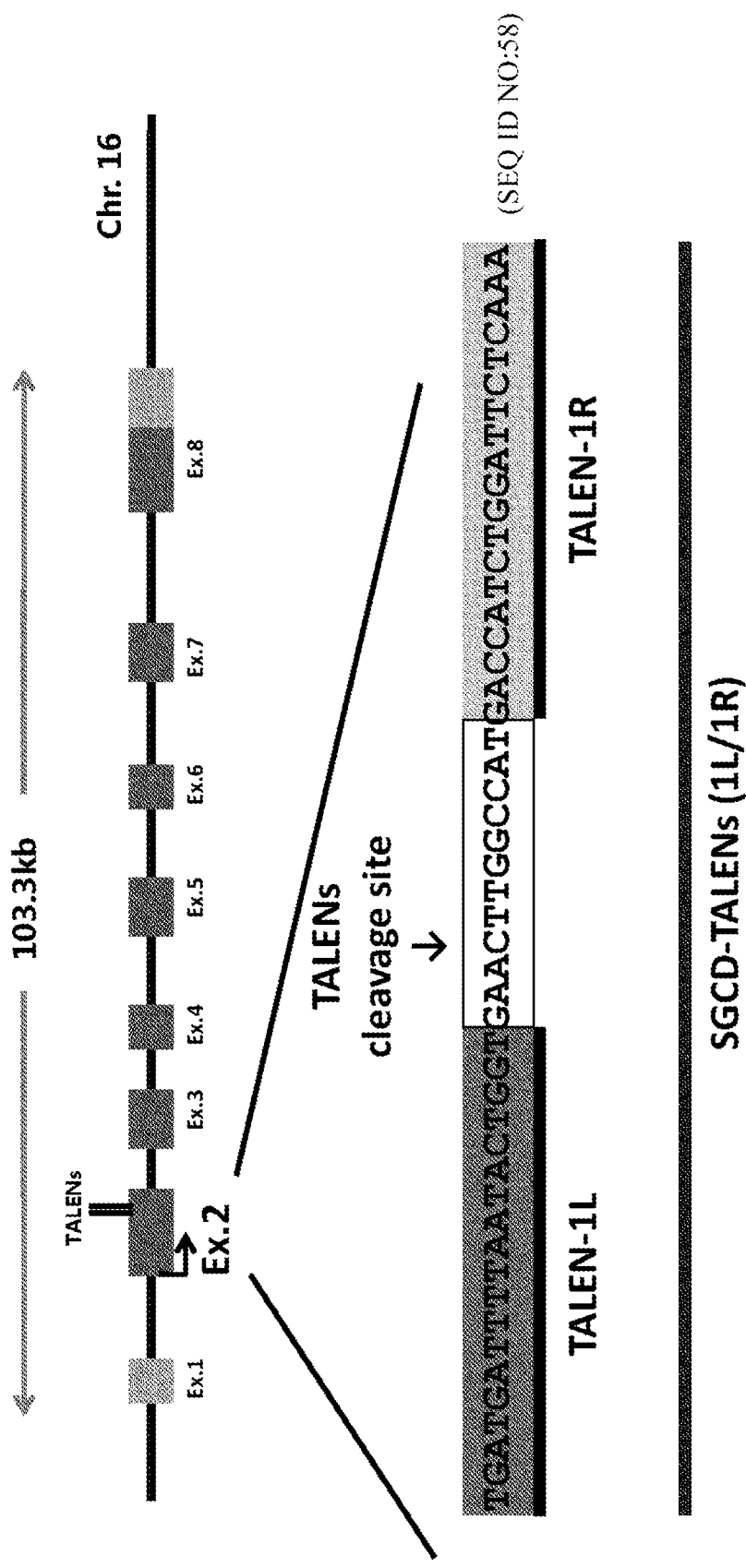
FIG. 5 is a drawing illustrating the structure of δ-sarcoglycan (SGCD) gene on the chromosome 16 of the pig and a modification technique of the SGCD gene (SEQ ID NO: 58) using the genome editing technique.

The disruption of the δ-sarcoglycan gene (SGCD) was conducted as follows. The pig SGCD gene locates on chromosome 16 and is considered to consist of 8 exons. In this Example, TALEN that targets the second exon including the start codon was constructed (FIG. 5).

The mRNA encoding TALEN was introduced into fetus fibroblasts of a male pig by electroporation. 185 clones obtained by limiting dilution of the cells were subsequently analyzed on the DNA sequence targeted by the TALEN and mutations were found in 67 clones (FIG. 6). Among obtained clones, the clone Nos. 26 had a 4 nucleotide deletion that creates a nonsense mutation and a 1859 nucleotide deletion that largely deletes the transmembrane domain important for the function of SGCD greatly in the second exon. The clone No. 49 had a 5 nucleotide deletion that creates a nonsense mutation and a 713 nucleotide deletion that completely deletes exon 2 in the second exon. It was considered that the function of the SGCD gene was disrupted in these clones.

Embryos were obtained by somatic cell cloning using the nuclei of these clones in the same way as Example 3 and SGCD gene knockout pigs were obtained. These offspring developed symptoms characteristic of dilated cardiomyopathy in 4 weeks after birth. The general symptoms of the offspring were severer than the symptoms estimated from patients with a usual SGCD gene deficiency and some individuals died of heart failure in several weeks after birth. Analysis of plural offspring revealed that the phenotypes were greatly different among individuals (Table 3).

TABLE 3

| | Individual No. | | | | | | | |
|---|---|---|---|---|---|---|---|---|
| | SGCD clone | | | | WT | | | |
| | #1 | #2 | #3 | Ave. | #1 | #2 | #3 | Ave. |
| Body weight (kg) | 5.6 | 9.8 | 9.3 | 8.2 | 13.3 | 14.5 | 15.4 | 14.4 |
| Left ventricular end-diastolic dimension [LVDd] (mm) | 27 | 31 | 28 | 28.7 [27-31] | 30 | 27 | 35 | 30.7 [27-35] |
| Left ventricular end-systolic dimension [LVDs] (mm) | 21 | 22 | 18 | 22.3 [18-28] | 14 | 13 | 17 | 14.7 [13-17] |
| Ventricular septum (mm) | 4 | 5 | 3 | 4.0 [3-5] | 6 | 7 | 7 | 6.7 [6-7] |
| Left ventricular posterior wall (mm) | 4 | 5 | 4 | 4.3 [4-5] | 6 | 6 | 7 | 6.3 [6-7] |
| Left ventricular ejection fraction [LVEF] (%) | 49 | 60 | 67 | 58.7 [49-67] | 85 | 85 | 82 | 84 [82-85] |
| Ventricular muscular fiber | Degeneration of the muscular fiber | | | | Normal | | | |
| Skeletal muscle | Muscular dystrophy-like degeneration | | | | Normal | | | |

In the same way as Example 3, a chimeric embryo of the obtained embryo and an embryo obtained by somatic cell cloning from a cell expressing Kusabira Orange was made and transplanted into a surrogate mother that underwent estrus synchronization and a chimeric individual was produced. The obtained chimeric individual was male. However, this male died before reaching sexual maturation. The cause of death was estimated to be arrhythmia by the stress of the administration of agents such as sedatives. Before the male pig died, its testicular tissue was collected and cryopreserved.

It is known that sperms having fertility can be obtained by transplanting a cryopreserved testicular tissue under skin of an immunodeficient mouse. Accordingly, obtaining the second generation offspring by fertilizing a wildtype female unfertilized egg with obtained sperms should provide female pigs having the SGCD gene deficiency on one of the chromosomes among offspring. Such female pigs will be carriers of the SGCD gene deficiency.

The third generation individuals can be obtained by subjecting unfertilized eggs obtained from such carriers to sexual reproduction with sperms obtained as described above. Among the third generation individuals, male individuals having the SGCD gene deficiency become model animals that reproduce the phenotype of human male patients born from mothers who are carriers of the SGCD gene deficiency.

Moreover, the obtained third generation individuals become model animals that closely reproduce the pathology free of the epigenetic effect present in the first generation, that is to say, the phenotype of human male patients born from mothers who are carriers.

It is likely that the aforementioned second generation pigs heterozygous for the SGCD gene deficiency will appear the pathology of dilated cardiomyopathy. Since the somatic epigenetic modification has been reset in the second generation pigs, as illustrated in Example 2, the second generation pigs are expected to exhibit pathologies closer to human patients with familial dilated cardiomyopathy patient.

The invention claimed is:

1. A method for producing a genetically modified pig, the method comprising:
   producing an enucleated pig oocyte by eliminating or inactivating a nucleus of a an unfertilized pig oocyte;
   transplanting a nucleus of a pig somatic cell having a genetic modification into cytoplasm of the enucleated pig oocyte, thereby obtaining a clonal embryo;
   mixing the clonal embryo with an embryo of a pig without a fetal genetic disease to yield a chimeric embryo;
   developing the chimeric embryo in the womb of a female to obtain a chimeric pig; and
   mating the chimeric pig or having the chimeric pig undergo sexual reproduction to obtain a genetically modified pig comprising in its genome the genetic modification present in the pig somatic cell,
   wherein the genetically modified pig further comprises a phenotype and said phenotype is more stable than said phenotype in a genetically modified pig obtained by developing the clonal embryo in the womb of a female to obtain a cloned pig.

2. The method of claim 1, wherein the genetically modified pig comprising in its genome the genetic modification present in the pig somatic cell is free of a nuclear-transfer, epigenetic effect present in a cloned pig.

3. A method of producing a pig, the method comprising:
   producing an enucleated pig oocyte by eliminating or inactivating a nucleus of an unfertilized pig oocyte;
   transplanting a nucleus of a pig somatic cell into cytoplasm of the enucleated pig oocyte thereby obtaining a clonal embryo;
   mixing the clonal embryo with an embryo of a pig without a fetal genetic disease to yield a chimeric embryo;
   developing the chimeric embryo in the womb of a female pig to obtained a first generation chimeric pig; and
   mating the chimeric pig or having the chimeric pig undergo sexual reproduction to further obtain a second generation pig that is free of a nuclear-transfer, epigenetic effect present in a cloned pig produced by developing the clonal embryo into a cloned pig.

* * * * *

SEQUENCE LISTING

```
<160> NUMBER OF SEQ ID NOS: 16

<210> SEQ ID NO 1
<211> LENGTH: 2351
<212> TYPE: DNA
<213> ORGANISM: Homo sapiens
<220> FEATURE:
<221> NAME/KEY: CDS
<222> LOCATION: (1)..(1893)
<220> FEATURE:
<221> NAME/KEY: misc_feature
<222> LOCATION: (965)..(965)
<223> OTHER INFORMATION: n is a, c, g, or t

<400> SEQUENCE: 1 atg gtt tct aaa ctg agc cag ctg cag acg gag ctc ctg gcg gcc ctg      48
Met Val Ser Lys Leu Ser Gln Leu Gln Thr Glu Leu Leu Ala Ala Leu
1               5                   10                  15 ctc gag tca ggg ctg agc aaa gag gca ctg atc cag gca ctg ggt gag      96
Leu Glu Ser Gly Leu Ser Lys Glu Ala Leu Ile Gln Ala Leu Gly Glu
                20                  25                  30 ccg ggg ccc tac ctc ctg gct gga gaa ggc ccc ctg gac aag ggg gag     144
Pro Gly Pro Tyr Leu Leu Ala Gly Glu Gly Pro Leu Asp Lys Gly Glu
            35                  40                  45 tcc tgc ggc ggc ggt cga ggg gag ctg gct gag ctg ccc aat ggg ctg     192
Ser Cys Gly Gly Gly Arg Gly Glu Leu Ala Glu Leu Pro Asn Gly Leu
        50                  55                  60 ggg gag act cgg ggc tcc gag gac gag acg gac gac gat ggg gaa gac     240
Gly Glu Thr Arg Gly Ser Glu Asp Glu Thr Asp Asp Asp Gly Glu Asp
65                  70                  75                  80 ttc acg cca ccc atc ctc aaa gag ctg gag aac ctc agc cct gag gag     288
Phe Thr Pro Pro Ile Leu Lys Glu Leu Glu Asn Leu Ser Pro Glu Glu
                85                  90                  95 gcg gcc cac cag aaa gcc gtg gtg gag acc ctt ctg cag gag gac ccg     336
Ala Ala His Gln Lys Ala Val Val Glu Thr Leu Leu Gln Glu Asp Pro
                100                 105                 110 tgg cgt gtg gcg aag atg gtc aag tcc tac ctg cag cag cac aac atc     384
Trp Arg Val Ala Lys Met Val Lys Ser Tyr Leu Gln Gln His Asn Ile
            115                 120                 125 cca cag cgg gag gtg gtc gat acc act ggc ctc aac cag tcc cac ctg     432
Pro Gln Arg Glu Val Val Asp Thr Thr Gly Leu Asn Gln Ser His Leu
        130                 135                 140 tcc caa cac ctc aac aag ggc act ccc atg aag acg cag aag cgg gcc     480
Ser Gln His Leu Asn Lys Gly Thr Pro Met Lys Thr Gln Lys Arg Ala
145                 150                 155                 160 gcc ctg tac acc tgg tac gtc cgc aag cag cga gag gtg gcg cag cag     528
Ala Leu Tyr Thr Trp Tyr Val Arg Lys Gln Arg Glu Val Ala Gln Gln
                165                 170                 175
```

```
ttc acc cat gca ggg cag gga ggg ctg att gaa gag ccc aca ggt gat      576
Phe Thr His Ala Gly Gln Gly Gly Leu Ile Glu Glu Pro Thr Gly Asp
            180                 185                 190 gag cta cca acc aag aag ggg cgg agg aac cgt ttc aag tgg ggc cca      624
Glu Leu Pro Thr Lys Lys Gly Arg Arg Asn Arg Phe Lys Trp Gly Pro
    195                 200                 205 gca tcc cag cag atc ctg ttc cag gcc tat gag agg cag aag aac cct      672
Ala Ser Gln Gln Ile Leu Phe Gln Ala Tyr Glu Arg Gln Lys Asn Pro
210                 215                 220 agc aag gag gag cga gag acg cta gtg gag gag tgc aat agg gcg gaa      720
Ser Lys Glu Glu Arg Glu Thr Leu Val Glu Glu Cys Asn Arg Ala Glu
225                 230                 235                 240 tgc atc cag aga ggg gtg tcc cca tca cag gca cag ggg ctg ggc tcc      768
Cys Ile Gln Arg Gly Val Ser Pro Ser Gln Ala Gln Gly Leu Gly Ser
            245                 250                 255 aac ctc gtc acg gag gtg cgt gtc tac aac tgg ttt gcc aac cgg cgc      816
Asn Leu Val Thr Glu Val Arg Val Tyr Asn Trp Phe Ala Asn Arg Arg
    260                 265                 270 aaa gaa gaa gcc ttc cgg cac aag ctg gcc atg gac acg tac agc ggg      864
Lys Glu Glu Ala Phe Arg His Lys Leu Ala Met Asp Thr Tyr Ser Gly
275                 280                 285 ccc ccc cca ggg cca ggc ccg gga cct gcg ctg ccc gct cac agc tcc      912
Pro Pro Pro Gly Pro Gly Pro Gly Pro Ala Leu Pro Ala His Ser Ser
290                 295                 300 cct ggc ctg cct cca cct gcc ctc tcc ccc agt aag gtc cac ggt gtg      960
Pro Gly Leu Pro Pro Pro Ala Leu Ser Pro Ser Lys Val His Gly Val
305                 310                 315                 320 cgc tnt gga cag cct gcg acc agt gag act gca gaa gta ccc tca agc     1008
Arg Xaa Gly Gln Pro Ala Thr Ser Glu Thr Ala Glu Val Pro Ser Ser
            325                 330                 335 agc ggc ggt ccc tta gtg aca gtg tct aca ccc ctc cac caa gtg tcc     1056
Ser Gly Gly Pro Leu Val Thr Val Ser Thr Pro Leu His Gln Val Ser
    340                 345                 350 ccc acg ggc ctg gag ccc agc cac agc ctg ctg agt aca gaa gcc aag     1104
Pro Thr Gly Leu Glu Pro Ser His Ser Leu Leu Ser Thr Glu Ala Lys
355                 360                 365 ctg gtc tca gca gct ggg ggc ccc ctc ccc cct gtc agc acc ctg aca     1152
Leu Val Ser Ala Ala Gly Gly Pro Leu Pro Pro Val Ser Thr Leu Thr
370                 375                 380 gca ctg cac agc ttg gag cag aca tcc cca ggc ctc aac cag cag ccc     1200
Ala Leu His Ser Leu Glu Gln Thr Ser Pro Gly Leu Asn Gln Gln Pro
385                 390                 395                 400 cag aac ctc atc atg gcc tca ctt cct ggg gtc atg acc atc ggg cct     1248
Gln Asn Leu Ile Met Ala Ser Leu Pro Gly Val Met Thr Ile Gly Pro
            405                 410                 415 ggt gag cct gcc tcc ctg ggt cct acg ttc acc aac aca ggt gcc tcc     1296
Gly Glu Pro Ala Ser Leu Gly Pro Thr Phe Thr Asn Thr Gly Ala Ser
    420                 425                 430 acc ctg gtc atc ggc ctg gcc tcc acg cag gca cag agt gtg ccg gtc     1344
Thr Leu Val Ile Gly Leu Ala Ser Thr Gln Ala Gln Ser Val Pro Val
435                 440                 445 atc aac agc atg ggc agc agc ctg acc acc ctg cag ccc gtc cag ttc     1392
Ile Asn Ser Met Gly Ser Ser Leu Thr Thr Leu Gln Pro Val Gln Phe
450                 455                 460 tcc cag ccg ctg cac ccc tcc tac cag cag ccg ctc atg cca cct gtg     1440
Ser Gln Pro Leu His Pro Ser Tyr Gln Gln Pro Leu Met Pro Pro Val
465                 470                 475                 480 cag agc cat gtg acc cag agc ccc ttc atg gcc acc atg gct cag ctg     1488
Gln Ser His Val Thr Gln Ser Pro Phe Met Ala Thr Met Ala Gln Leu
            485                 490                 495
```

```
cag agc ccc cac gcc ctc tac agc cac aag ccc gag gtg gcc cag tac    1536
Gln Ser Pro His Ala Leu Tyr Ser His Lys Pro Glu Val Ala Gln Tyr
            500                 505                 510 acc cac acg ggc ctg ctc ccg cag act atg ctc atc acc gac acc acc    1584
Thr His Thr Gly Leu Leu Pro Gln Thr Met Leu Ile Thr Asp Thr Thr
        515                 520                 525 aac ctg agc gcc ctg gcc agc ctc acg ccc acc aag cag gtc ttc acc    1632
Asn Leu Ser Ala Leu Ala Ser Leu Thr Pro Thr Lys Gln Val Phe Thr
    530                 535                 540 tca gac act gag gcc tcc agt gag tcc ggg ctt cac acg ccg gca tct    1680
Ser Asp Thr Glu Ala Ser Ser Glu Ser Gly Leu His Thr Pro Ala Ser
545                 550                 555                 560 cag gcc acc acc ctc cac gtc ccc agc cag gac cct gcc ggc atc cag    1728
Gln Ala Thr Thr Leu His Val Pro Ser Gln Asp Pro Ala Gly Ile Gln
                565                 570                 575 cac ctg cag ccg gcc cac cgg ctc agc gcc agc ccc aca gtg tcc tcc    1776
His Leu Gln Pro Ala His Arg Leu Ser Ala Ser Pro Thr Val Ser Ser
            580                 585                 590 agc agc ctg gtg ctg tac cag agc tca gac tcc agc aat ggc cag agc    1824
Ser Ser Leu Val Leu Tyr Gln Ser Ser Asp Ser Ser Asn Gly Gln Ser
        595                 600                 605 cac ctg ctg cca tcc aac cac agc gtc atc gag acc ttc atc tcc acc    1872
His Leu Leu Pro Ser Asn His Ser Val Ile Glu Thr Phe Ile Ser Thr
    610                 615                 620 cag atg gcc tct tcc tcc cag taaccacggc acctgggccc tggggcctgt       1923
Gln Met Ala Ser Ser Ser Gln
625                 630 actgcctgct tggggggtga tgagggcagc agccagccct gcctggagga cctgagcctg  1983
ccgagcaacc gtggcccttc ctggacagct gtgcctcgct ccccactctg ctctgatgca  2043
tcagaaaggg agggctctga ggcgcccaa cccgtggagg ctgctcgggg tgcacaggag   2103
ggggtcgtgg agagctagga gcaaagcctg ttcatggcag atgtaggagg gactgtcgct  2163
gcttcgtggg atacagtctt cttacttgga actgaagggg gcggcctatg acttgggcac  2223
ccccagcctg ggcctatgga gagccctggg accgctacac cactctggca gccacacttc  2283
tcaggacaca ggcctgtgta gctgtgacct gctgagctct gagaggccct ggatcagcgt  2343
ggccttgt                                                          2351
```

<210> SEQ ID NO 2
<211> LENGTH: 631
<212> TYPE: PRT
<213> ORGANISM: Homo sapiens
<220> FEATURE:
<221> NAME/KEY: misc_feature
<222> LOCATION: (322)..(322)
<223> OTHER INFORMATION: The 'Xaa' at location 322 stands for Tyr, Cys,
      Ser, or Phe.

<400> SEQUENCE: 2

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp

```
                65                  70                  75                  80
           Phe Thr Pro Pro Ile Leu Lys Glu Leu Glu Asn Leu Ser Pro Glu Glu
                               85                  90                  95

Ala Ala His Gln Lys Ala Val Val Glu Thr Leu Leu Gln Glu Asp Pro
                              100                 105                 110

Trp Arg Val Ala Lys Met Val Lys Ser Tyr Leu Gln His Asn Ile
                              115                 120                 125

Pro Gln Arg Glu Val Val Asp Thr Thr Gly Leu Asn Gln Ser His Leu
                              130                 135                 140

Ser Gln His Leu Asn Lys Gly Thr Pro Met Lys Thr Gln Lys Arg Ala
           145                 150                 155                 160

Ala Leu Tyr Thr Trp Tyr Val Arg Lys Gln Arg Glu Val Ala Gln Gln
                              165                 170                 175

Phe Thr His Ala Gly Gln Gly Gly Leu Ile Glu Glu Pro Thr Gly Asp
                              180                 185                 190

Glu Leu Pro Thr Lys Lys Gly Arg Arg Asn Arg Phe Lys Trp Gly Pro
                              195                 200                 205

Ala Ser Gln Gln Ile Leu Phe Gln Ala Tyr Glu Arg Gln Lys Asn Pro
                              210                 215                 220

Ser Lys Glu Glu Arg Glu Thr Leu Val Glu Glu Cys Asn Arg Ala Glu
           225                 230                 235                 240

Cys Ile Gln Arg Gly Val Ser Pro Ser Gln Ala Gln Gly Leu Gly Ser
                              245                 250                 255

Asn Leu Val Thr Glu Val Arg Val Tyr Asn Trp Phe Ala Asn Arg Arg
                              260                 265                 270

Lys Glu Glu Ala Phe Arg His Lys Leu Ala Met Asp Thr Tyr Ser Gly
                              275                 280                 285

Pro Pro Pro Gly Pro Gly Pro Gly Pro Ala Leu Pro Ala His Ser Ser
                              290                 295                 300

Pro Gly Leu Pro Pro Pro Ala Leu Ser Pro Ser Lys Val His Gly Val
           305                 310                 315                 320

Arg Xaa Gly Gln Pro Ala Thr Ser Glu Thr Ala Glu Val Pro Ser Ser
                              325                 330                 335

Ser Gly Gly Pro Leu Val Thr Val Ser Thr Pro Leu His Gln Val Ser
                              340                 345                 350

Pro Thr Gly Leu Glu Pro Ser His Ser Leu Leu Ser Thr Glu Ala Lys
                              355                 360                 365

Leu Val Ser Ala Ala Gly Gly Pro Leu Pro Pro Val Ser Thr Leu Thr
                              370                 375                 380

Ala Leu His Ser Leu Glu Gln Thr Ser Pro Gly Leu Asn Gln Gln Pro
           385                 390                 395                 400

Gln Asn Leu Ile Met Ala Ser Leu Pro Gly Val Met Thr Ile Gly Pro
                              405                 410                 415

Gly Glu Pro Ala Ser Leu Gly Pro Thr Phe Thr Asn Thr Gly Ala Ser
                              420                 425                 430

Thr Leu Val Ile Gly Leu Ala Ser Thr Gln Ala Gln Ser Val Pro Val
                              435                 440                 445

Ile Asn Ser Met Gly Ser Ser Leu Thr Thr Leu Gln Pro Val Gln Phe
                              450                 455                 460

Ser Gln Pro Leu His Pro Ser Tyr Gln Gln Pro Leu Met Pro Pro Val
           465                 470                 475                 480

Gln Ser His Val Thr Gln Ser Pro Phe Met Ala Thr Met Ala Gln Leu
                              485                 490                 495
```

```
Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
            515                 520                 525

Asn Leu Ser Ala Leu Ala Ser Leu Thr Pro Thr Lys Gln Val Phe Thr
            530                 535                 540

Ser Asp Thr Glu Ala Ser Ser Glu Ser Gly Leu His Thr Pro Ala Ser
545                 550                 555                 560

Gln Ala Thr Thr Leu His Val Pro Ser Gln Asp Pro Ala Gly Ile Gln
            565                 570                 575

His Leu Gln Pro Ala His Arg Leu Ser Ala Ser Pro Thr Val Ser Ser
            580                 585                 590

Ser Ser Leu Val Leu Tyr Gln Ser Ser Asp Ser Ser Asn Gly Gln Ser
            595                 600                 605

His Leu Leu Pro Ser Asn His Ser Val Ile Glu Thr Phe Ile Ser Thr
            610                 615                 620

Gln Met Ala Ser Ser Ser Gln
625                 630

<210> SEQ ID NO 3
<211> LENGTH: 2352
<212> TYPE: DNA
<213> ORGANISM: Homo sapiens
<220> FEATURE:
<221> NAME/KEY: CDS
<222> LOCATION: (1)..(945)
<220> FEATURE:
<221> NAME/KEY: misc_feature
<222> LOCATION: (966)..(966)
<223> OTHER INFORMATION: n is a, c, g, or t

<400> SEQUENCE: 3 atg gtt tct aaa ctg agc cag ctg cag acg gag ctc ctg gcg gcc ctg      48
Met Val Ser Lys Leu Ser Gln Leu Gln Thr Glu Leu Leu Ala Ala Leu
1               5                   10                  15 ctc gag tca ggg ctg agc aaa gag gca ctg atc cag gca ctg ggt gag      96
Leu Glu Ser Gly Leu Ser Lys Glu Ala Leu Ile Gln Ala Leu Gly Glu
                20                  25                  30 ccg ggg ccc tac ctc ctg gct gga gaa ggc ccc ctg gac aag ggg gag     144
Pro Gly Pro Tyr Leu Leu Ala Gly Glu Gly Pro Leu Asp Lys Gly Glu
            35                  40                  45 tcc tgc ggc ggc ggt cga ggg gag ctg gct gag ctg ccc aat ggg ctg     192
Ser Cys Gly Gly Gly Arg Gly Glu Leu Ala Glu Leu Pro Asn Gly Leu
        50                  55                  60 ggg gag act cgg ggc tcc gag gac gag acg gac gac gat ggg gaa gac     240
Gly Glu Thr Arg Gly Ser Glu Asp Glu Thr Asp Asp Asp Gly Glu Asp
65                  70                  75                  80 ttc acg cca ccc atc ctc aaa gag ctg gag aac ctc agc cct gag gag     288
Phe Thr Pro Pro Ile Leu Lys Glu Leu Glu Asn Leu Ser Pro Glu Glu
                85                  90                  95 gcg gcc cac cag aaa gcc gtg gtg gag acc ctt ctg cag gag gac ccg     336
Ala Ala His Gln Lys Ala Val Val Glu Thr Leu Leu Gln Glu Asp Pro
            100                 105                 110 tgg cgt gtg gcg aag atg gtc aag tcc tac ctg cag cag cac aac atc     384
Trp Arg Val Ala Lys Met Val Lys Ser Tyr Leu Gln Gln His Asn Ile
        115                 120                 125 cca cag cgg gag gtg gtc gat acc act ggc ctc aac cag tcc cac ctg     432
Pro Gln Arg Glu Val Val Asp Thr Thr Gly Leu Asn Gln Ser His Leu
    130                 135                 140
```

```
tcc caa cac ctc aac aag ggc act ccc atg aag acg cag aag cgg gcc    480
Ser Gln His Leu Asn Lys Gly Thr Pro Met Lys Thr Gln Lys Arg Ala
145                 150                 155                 160 gcc ctg tac acc tgg tac gtc cgc aag cag cga gag gtg gcg cag cag    528
Ala Leu Tyr Thr Trp Tyr Val Arg Lys Gln Arg Glu Val Ala Gln Gln
                165                 170                 175 ttc acc cat gca ggg cag gga ggg ctg att gaa gag ccc aca ggt gat    576
Phe Thr His Ala Gly Gln Gly Gly Leu Ile Glu Glu Pro Thr Gly Asp
            180                 185                 190 gag cta cca acc aag aag ggg cgg agg aac cgt ttc aag tgg ggc cca    624
Glu Leu Pro Thr Lys Lys Gly Arg Arg Asn Arg Phe Lys Trp Gly Pro
        195                 200                 205 gca tcc cag cag atc ctg ttc cag gcc tat gag agg cag aag aac cct    672
Ala Ser Gln Gln Ile Leu Phe Gln Ala Tyr Glu Arg Gln Lys Asn Pro
    210                 215                 220 agc aag gag gag cga gag acg cta gtg gag gag tgc aat agg gcg gaa    720
Ser Lys Glu Glu Arg Glu Thr Leu Val Glu Glu Cys Asn Arg Ala Glu
225                 230                 235                 240 tgc atc cag aga ggg gtg tcc cca tca cag gca cag ggg ctg ggc tcc    768
Cys Ile Gln Arg Gly Val Ser Pro Ser Gln Ala Gln Gly Leu Gly Ser
                245                 250                 255 aac ctc gtc acg gag gtg cgt gtc tac aac tgg ttt gcc aac cgg cgc    816
Asn Leu Val Thr Glu Val Arg Val Tyr Asn Trp Phe Ala Asn Arg Arg
            260                 265                 270 aaa gaa gaa gcc ttc cgg cac aag ctg gcc atg gac acg tac agc ggg    864
Lys Glu Glu Ala Phe Arg His Lys Leu Ala Met Asp Thr Tyr Ser Gly
        275                 280                 285 ccc ccc ccc agg gcc agg ccc ggg acc tgc gct gcc cgc tca cag ctc    912
Pro Pro Pro Arg Ala Arg Pro Gly Thr Cys Ala Ala Arg Ser Gln Leu
    290                 295                 300 ccc tgg cct gcc tcc acc tgc cct ctc ccc cag taaggtccac ggtgtgcgct  965
Pro Trp Pro Ala Ser Thr Cys Pro Leu Pro Gln
305                 310                 315 ntggacagcc tgcgaccagt gagactgcag aagtaccctc aagcagcggc ggtcccttag 1025 tgacagtgtc tacaccctc caccaagtgt ccccacggg cctggagccc agccacagcc  1085
tgctgagtac agaagccaag ctggtctcag cagctggggg ccccctcccc cctgtcagca 1145 ccctgacagc actgcacagc ttggagcaga catccccagg cctcaaccag cagccccaga 1205 acctcatcat ggcctcactt cctggggtca tgaccatcgg gctggtgag cctgcctccc  1265 tgggtcctac gttcaccaac acaggtgcct ccaccctggt catcggcctg gcctccacgc 1325 aggcacagag tgtgccggtc atcaacagca tgggcagcag cctgaccacc ctgcagcccg 1385 tccagttctc ccagccgctg caccctcct accagcagcc gctcatgcca cctgtgcaga 1445 gccatgtgac ccagagcccc ttcatggcca ccatggctca gctgcagagc ccccacgccc 1505 tctacagcca caagcccgag gtggcccagt acacccacac gggcctgctc ccgcagacta 1565 tgctcatcac cgacaccacc aacctgagcg ccctggccag cctcacgccc accaagcagg 1625 tcttcacctc agacactgag gcctccagtg agtccgggct tcacacgccg gcatctcagg 1685 ccaccaccct ccacgtcccc agccaggacc ctgccggcat ccagcacctg cagccggccc 1745 accggctcag cgccagcccc acagtgtcct ccagcagcct ggtgctgtac cagagctcag 1805 actccagcaa tggccagagc cacctgctgc catccaacca cagcgtcatc gagaccttca 1865 tctccaccca gatggcctct tcctcccagt aaccacggca cctgggccct ggggcctgta 1925 ctgcctgctt gggggtgat gagggcagca gccagccctg cctggaggac ctgagcctgc 1985 cgagcaaccg tggcccttcc tggacagctg tgcctcgctc cccactctgc tctgatgcat 2045
```

```
cagaaaggga gggctctgag gcgccccaac ccgtggaggc tgctcggggt gcacaggagg   2105
gggtcgtgga gagctaggag caaagcctgt tcatggcaga tgtaggaggg actgtcgctg   2165
cttcgtggga tacagtcttc ttacttggaa ctgaaggggg cggcctatga cttgggcacc   2225
cccagcctgg gcctatggag agccctggga ccgctacacc actctggcag ccacacttct   2285
caggacacag gcctgtgtag ctgtgacctg ctgagctctg agaggccctg gatcagcgtg   2345
gccttgt                                                             2352
```

<210> SEQ ID NO 4
<211> LENGTH: 315
<212> TYPE: PRT
<213> ORGANISM: Homo sapiens

<400> SEQUENCE: 4

```
Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
        275                 280                 285

Pro Pro Pro Arg Ala Arg Pro Gly Thr Cys Ala Ala Arg Ser Gln Leu
    290                 295                 300

Pro Trp Pro Ala Ser Thr Cys Pro Leu Pro Gln
305                 310                 315
```

<210> SEQ ID NO 5
<211> LENGTH: 2006
<212> TYPE: DNA
<213> ORGANISM: Sus scrofa
<220> FEATURE:
<221> NAME/KEY: CDS
<222> LOCATION: (42)..(1106)

<400> SEQUENCE: 5

```
tttcaagagc ccagacgcat cctttcacc atcaaaggaa g atg ctg ttt aat ttg      56
                                             Met Leu Phe Asn Leu
                                             1               5 agg att ctg ttg aac aag tca gcc ctt aga cac agt cac aat tgc gtg      104
Arg Ile Leu Leu Asn Lys Ser Ala Leu Arg His Ser His Asn Cys Val
            10                  15                  20 gtg cga aat ttt cga tgt gga caa cca cta caa aat aaa gtg cag ctg      152
Val Arg Asn Phe Arg Cys Gly Gln Pro Leu Gln Asn Lys Val Gln Leu
        25                  30                  35 aag ggt cgt gac ctc ctc act cta aag aac ttt aca gga gaa gaa att      200
Lys Gly Arg Asp Leu Leu Thr Leu Lys Asn Phe Thr Gly Glu Glu Ile
    40                  45                  50 aag tat atc cta tgg cta tca gct gat ctg aaa ttt agg ata aag cag      248
Lys Tyr Ile Leu Trp Leu Ser Ala Asp Leu Lys Phe Arg Ile Lys Gln
55                  60                  65 aaa gga gag tat ttg cct tta ttg caa ggg aag tcc ctc ggc atg att      296
Lys Gly Glu Tyr Leu Pro Leu Leu Gln Gly Lys Ser Leu Gly Met Ile
70                  75                  80                  85 ttt gaa aaa aga agt act cga aca aga ttg tct aca gaa aca ggc ttt      344
Phe Glu Lys Arg Ser Thr Arg Thr Arg Leu Ser Thr Glu Thr Gly Phe
                90                  95                  100 gcc ctt cta gga gga cac cct tgt ttt ctt acc aca caa gat att cac      392
Ala Leu Leu Gly Gly His Pro Cys Phe Leu Thr Thr Gln Asp Ile His
            105                 110                 115 ttg ggt gtg aat gaa agt ctc aag gac acc gct cgt gtg ttg tct agc      440
Leu Gly Val Asn Glu Ser Leu Lys Asp Thr Ala Arg Val Leu Ser Ser
        120                 125                 130 atg aca gat gca gtg ttg gcg cga gtg tat aaa caa tca gac ctg gac      488
Met Thr Asp Ala Val Leu Ala Arg Val Tyr Lys Gln Ser Asp Leu Asp
    135                 140                 145 atc ctg gct caa gaa gca tcc atc cca atc atc aat ggg ctg tca gat      536
Ile Leu Ala Gln Glu Ala Ser Ile Pro Ile Ile Asn Gly Leu Ser Asp
150                 155                 160                 165 ttg tac cat cct atc cag atc ctg gct gat tac ctc acg ctc cag gaa      584
Leu Tyr His Pro Ile Gln Ile Leu Ala Asp Tyr Leu Thr Leu Gln Glu
                170                 175                 180 cac tac ggc gct ctg aaa ggc ctt acc ctc agc tgg att ggg gat ggg      632
His Tyr Gly Ala Leu Lys Gly Leu Thr Leu Ser Trp Ile Gly Asp Gly
            185                 190                 195 aat aac atc ctg cac tcc atc atg atg agt gcg gcg aaa ttt ggg atg      680
Asn Asn Ile Leu His Ser Ile Met Met Ser Ala Ala Lys Phe Gly Met
        200                 205                 210 cac ctt cag gtg gcg act cca aag ggc tat gag ccg gat ccc agt ata      728
His Leu Gln Val Ala Thr Pro Lys Gly Tyr Glu Pro Asp Pro Ser Ile
    215                 220                 225 acc aag ttg gcg gag cag tat gcc aag gag aac ggg acc aag ctg tcg      776
Thr Lys Leu Ala Glu Gln Tyr Ala Lys Glu Asn Gly Thr Lys Leu Ser
230                 235                 240                 245 ctg acg aat gat cca ttg gag gcg gct cgt gga ggc aat gta tta att      824
Leu Thr Asn Asp Pro Leu Glu Ala Ala Arg Gly Gly Asn Val Leu Ile
```

```
                        250                 255                 260
aca gac act tgg ata agc atg gga caa gaa gag gag aag aaa aag cgg       872
Thr Asp Thr Trp Ile Ser Met Gly Gln Glu Glu Glu Lys Lys Lys Arg
            265                 270                 275 ctc cag gct ttc caa ggt tac cag gtt aca atg aag act gcg gaa gtt       920
Leu Gln Ala Phe Gln Gly Tyr Gln Val Thr Met Lys Thr Ala Glu Val
        280                 285                 290 gct gcc tct gac tgg aca ttt tta cac tgc ctg ccc aga aag cca gaa       968
Ala Ala Ser Asp Trp Thr Phe Leu His Cys Leu Pro Arg Lys Pro Glu
    295                 300                 305 gaa gtg gac gat gaa gtg ttt tac tct cca caa tca ctt gta ttc ccg      1016
Glu Val Asp Asp Glu Val Phe Tyr Ser Pro Gln Ser Leu Val Phe Pro
310                 315                 320                 325 gag gct gaa aac aga aag tgg aca atc atg gct gtc atg gtg tct ctg      1064
Glu Ala Glu Asn Arg Lys Trp Thr Ile Met Ala Val Met Val Ser Leu
                330                 335                 340 ctg aca gat tac tcg cct cag ctc cag aag ccg aag ttt tga              1106
Leu Thr Asp Tyr Ser Pro Gln Leu Gln Lys Pro Lys Phe
            345                 350
```

```
tgccgtgatg cttgtcaaga gggaaaccat gttctcccat aacagaatga gtcagttgat    1166
aagggaagga gaagagaatc taagaaataa acagatcctg atgcatggta tgggtgaatg    1226
atatgatatt gctttgccat tgtgaaacct ccctaaagcc cttaatttaa gtgcttgtgc    1286
actgtcatat gtggcttaac ttggtttaaa cttttccaatt cacaatttct gagttacatt   1346
tgggtatcat attaataacc atatacattt gcttcaacta acataaaat actgcgttca     1406
taacacataa tgcctaagcc attaaatgta atctatgctt attgccttaa taaattatca    1466
cccacgctaa tttataagta aacatttacc aggcagtcag ctgctggtag atctgtgggc    1526
tgtgctcgta tcccccagga ccaacaagga agctaaatga tccatcttgc tgatgtagtg    1586
caattttcag gcaaatgagg tagacagaca ttcatgtgcg gaggaaatga tgaaattctt    1646
agacaacaac tataatggtg tccaaactct ggagtttttt ccagtcattt ggggaaagag    1706
ggtccttgga gagcacacat ctctttctta taatgaatac ttaatgtaac aaacctaaag    1766
aagcctttgt gaacaaggtg gtagaaccat gcctatgtag ctaggaacat aagatccatt    1826
agtgacacct ttgtaggttc aaattctcca gcaggagaaa tttaattttt tcatgtctgt    1886
gcttgtcatg catctcatca caccacacac gggatagttc cataaattta ctgcttgcca    1946
catttcagcc cattttcccc tctaattttt cttcaagata ataaaatttt gctttactgg    2006
```

<210> SEQ ID NO 6
<211> LENGTH: 354
<212> TYPE: PRT
<213> ORGANISM: Sus scrofa

<400> SEQUENCE: 6

```
Met Leu Phe Asn Leu Arg Ile Leu Leu Asn Lys Ser Ala Leu Arg His
1               5                   10                  15

Ser His Asn Cys Val Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Ile Leu Trp Leu Ser Ala Asp Leu Lys
    50                  55                  60

Phe Arg Ile Lys Gln Lys Gly Glu Tyr Leu Pro Leu Leu Gln Gly Lys
65                  70                  75                  80
```

Ser Leu Gly Met Ile Phe Glu Lys Arg Ser Thr Arg Thr Arg Leu Ser
            85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Lys Asp Thr Ala
            115                 120                 125

Arg Val Leu Ser Ser Met Thr Asp Ala Val Leu Ala Arg Val Tyr Lys
            130                 135                 140

Gln Ser Asp Leu Asp Ile Leu Ala Gln Glu Ala Ser Ile Pro Ile Ile
145                 150                 155                 160

Asn Gly Leu Ser Asp Leu Tyr His Pro Ile Gln Ile Leu Ala Asp Tyr
            165                 170                 175

Leu Thr Leu Gln Glu His Tyr Gly Ala Leu Lys Gly Leu Thr Leu Ser
            180                 185                 190

Trp Ile Gly Asp Gly Asn Asn Ile Leu His Ser Ile Met Met Ser Ala
            195                 200                 205

Ala Lys Phe Gly Met His Leu Gln Val Ala Thr Pro Lys Gly Tyr Glu
            210                 215                 220

Pro Asp Pro Ser Ile Thr Lys Leu Ala Glu Gln Tyr Ala Lys Glu Asn
225                 230                 235                 240

Gly Thr Lys Leu Ser Leu Thr Asn Asp Pro Leu Glu Ala Ala Arg Gly
            245                 250                 255

Gly Asn Val Leu Ile Thr Asp Thr Trp Ile Ser Met Gly Gln Glu Glu
            260                 265                 270

Glu Lys Lys Lys Arg Leu Gln Ala Phe Gln Gly Tyr Gln Val Thr Met
            275                 280                 285

Lys Thr Ala Glu Val Ala Ala Ser Asp Trp Thr Phe Leu His Cys Leu
290                 295                 300

Pro Arg Lys Pro Glu Glu Val Asp Asp Glu Val Phe Tyr Ser Pro Gln
305                 310                 315                 320

Ser Leu Val Phe Pro Glu Ala Glu Asn Arg Lys Trp Thr Ile Met Ala
            325                 330                 335

Val Met Val Ser Leu Leu Thr Asp Tyr Ser Pro Gln Leu Gln Lys Pro
            340                 345                 350

Lys Phe

<210> SEQ ID NO 7
<211> LENGTH: 139
<212> TYPE: DNA
<213> ORGANISM: Sus scrofa

<400> SEQUENCE: 7
atgtggacaa ccactacaaa ataaagtgca gctgaagggt cgtgacctcc tcactctaaa      60
gaactttaca ggagaagaaa ttaagtatat cctatggcta tcagctgatc tgaaatttag     120
gataaagcag aaaggagag                                                  139

<210> SEQ ID NO 8
<211> LENGTH: 134
<212> TYPE: DNA
<213> ORGANISM: Sus scrofa

<400> SEQUENCE: 8
atgtggacaa ccactacaaa ataaagtgca gctgaagggt cgtgacctcc tcactctaaa      60
gaactttaca ggagaagaaa ttaagtatat cctatggcta tcagctgaaa tttaggataa     120
agcagaaagg agag                                                                     134

<210> SEQ ID NO 9
<211> LENGTH: 354
<212> TYPE: PRT
<213> ORGANISM: Sus scrofa

<400> SEQUENCE: 9

Met Leu Phe Asn Leu Arg Ile Leu Leu Asn Lys Ser Ala Leu Arg His
1               5                   10                  15

Ser His Asn Cys Val Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Ile Leu Trp Leu Ser Ala Asp Leu Lys
50                  55                  60

Phe Arg Ile Lys Gln Lys Gly Glu Tyr Leu Pro Leu Gln Gly Lys
65                  70                  75                  80

Ser Leu Gly Met Ile Phe Glu Lys Arg Ser Thr Arg Thr Arg Leu Ser
            85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Lys Asp Thr Ala
        115                 120                 125

Arg Val Leu Ser Ser Met Thr Asp Ala Val Leu Ala Arg Val Tyr Lys
130                 135                 140

Gln Ser Asp Leu Asp Ile Leu Ala Gln Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Gly Ala Leu Lys Gly Leu Thr Leu Ser
            180                 185                 190

Trp Ile Gly Asp Gly Asn Asn Ile Leu His Ser Ile Met Met Ser Ala
        195                 200                 205

Ala Lys Phe Gly Met His Leu Gln Val Ala Thr Pro Lys Gly Tyr Glu
    210                 215                 220

Pro Asp Pro Ser Ile Thr Lys Leu Ala Glu Gln Tyr Ala Lys Glu Asn
225                 230                 235                 240

Gly Thr Lys Leu Ser Leu Thr Asn Asp Pro Leu Glu Ala Ala Arg Gly
                245                 250                 255

Gly Asn Val Leu Ile Thr Asp Thr Trp Ile Ser Met Gly Gln Glu Glu
            260                 265                 270

Glu Lys Lys Lys Arg Leu Gln Ala Phe Gln Gly Tyr Gln Val Thr Met
        275                 280                 285

Lys Thr Ala Glu Val Ala Ala Ser Asp Trp Thr Phe Leu His Cys Leu
290                 295                 300

Pro Arg Lys Pro Glu Glu Val Asp Asp Glu Val Phe Tyr Ser Pro Gln
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
            340                 345                 350

Lys Phe

```
<210> SEQ ID NO 10
<211> LENGTH: 63
<212> TYPE: PRT
<213> ORGANISM: Sus scrofa

<400> SEQUENCE: 10

Met Leu Phe Asn Leu Arg Ile Leu Leu Asn Lys Ser Ala Leu Arg His
1               5                   10                  15

Ser His Asn Cys Val Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Ile Leu Trp Leu Ser Ala Glu Ile
    50                  55                  60

<210> SEQ ID NO 11
<211> LENGTH: 1068
<212> TYPE: DNA
<213> ORGANISM: Sus scrofa
<220> FEATURE:
<221> NAME/KEY: CDS
<222> LOCATION: (77)..(946)

<400> SEQUENCE: 11
ttccagcctc tccacacacg cctcctggac tgtgcggggt tctcaccagc cgctttgtgc         60
gaagaagaca agagag atg cct cag gaa cag tac aca cac cac cgg agc acc        112
                  Met Pro Gln Glu Gln Tyr Thr His His Arg Ser Thr
                  1               5                   10 atg ccc agc tcc gag ggg cca cag gta tac aaa gta ggg att tac ggc          160
Met Pro Ser Ser Glu Gly Pro Gln Val Tyr Lys Val Gly Ile Tyr Gly
            15                  20                  25 tgg cgg aaa aga tgc ttg tat ttc ttt gtc cta ctc ctg atg att tta          208
Trp Arg Lys Arg Cys Leu Tyr Phe Phe Val Leu Leu Leu Met Ile Leu
        30                  35                  40 ata ctg gtg aac ttg gcc atg acc atc tgg att ctc aaa gtc atg aac          256
Ile Leu Val Asn Leu Ala Met Thr Ile Trp Ile Leu Lys Val Met Asn
45                  50                  55                  60 ttc aca att gat gga atg gga aac ttg aga atc aca gaa aaa ggt cta          304
Phe Thr Ile Asp Gly Met Gly Asn Leu Arg Ile Thr Glu Lys Gly Leu
                65                  70                  75 aag tta gaa gga gac tca gaa ttc cta caa cct ctg tac gcc aaa gaa          352
Lys Leu Glu Gly Asp Ser Glu Phe Leu Gln Pro Leu Tyr Ala Lys Glu
            80                  85                  90 atc cag tcc cga cca ggt aat gcc ctg tac ttc aaa tct gcc aga aat          400
Ile Gln Ser Arg Pro Gly Asn Ala Leu Tyr Phe Lys Ser Ala Arg Asn
        95                  100                 105 gtt act gtg aac atc ctc aat gaa cag act aaa gtg cta act cag ctg          448
Val Thr Val Asn Ile Leu Asn Glu Gln Thr Lys Val Leu Thr Gln Leu
    110                 115                 120 ata aca ggt cca aat gcc ata gaa gct tat ggc aaa aag ttt gaa gta          496
Ile Thr Gly Pro Asn Ala Ile Glu Ala Tyr Gly Lys Lys Phe Glu Val
125                 130                 135                 140 aag acg gtt tct gga aaa ttg ctc ttc tct gca gat aac aat gaa gtc          544
Lys Thr Val Ser Gly Lys Leu Leu Phe Ser Ala Asp Asn Asn Glu Val
                145                 150                 155 gta gtg gga gct gaa aga ttg aga gtt tta gga gca gag ggc aca gtg          592
Val Val Gly Ala Glu Arg Leu Arg Val Leu Gly Ala Glu Gly Thr Val
            160                 165                 170 ttc cct aaa tct ata gag aca cct aat gtc agg gca gac ccc ttc aag          640
Phe Pro Lys Ser Ile Glu Thr Pro Asn Val Arg Ala Asp Pro Phe Lys
        175                 180                 185
```

```
gaa cta agg ttg gaa tcc ccc acc cgg tct ctg gtg atg gaa gcc cca      688
Glu Leu Arg Leu Glu Ser Pro Thr Arg Ser Leu Val Met Glu Ala Pro
    190                 195                 200 aaa gga gta gaa ata aat gca gaa gcc ggc aat atg gaa gcc acc tgc      736
Lys Gly Val Glu Ile Asn Ala Glu Ala Gly Asn Met Glu Ala Thr Cys
205                 210                 215                 220 aga aca gag ctg aga ctg gag tcc aaa gat gga gag att aag tta gat      784
Arg Thr Glu Leu Arg Leu Glu Ser Lys Asp Gly Glu Ile Lys Leu Asp
                225                 230                 235 gct gcg aaa atc aaa cta ccc aga ttg cct cac gga tcc tac aca ccc      832
Ala Ala Lys Ile Lys Leu Pro Arg Leu Pro His Gly Ser Tyr Thr Pro
        240                 245                 250 gcg gga acg agg cag aag gtc ttc gag atc tgc gtt tgt gcc aac ggg      880
Ala Gly Thr Arg Gln Lys Val Phe Glu Ile Cys Val Cys Ala Asn Gly
            255                 260                 265 aga tta ttc ctg tca cag gca gga act ggt tcc act tgt cag ata aac      928
Arg Leu Phe Leu Ser Gln Ala Gly Thr Gly Ser Thr Cys Gln Ile Asn
                270                 275                 280 aca agt gtc tgc ctg tga gagactatcc atagtggaca ctgtcgcagc             976
Thr Ser Val Cys Leu
285 ataaaggcct ttttggctt tagaccctgg ctgccagcta tttttactat aacacagaaa    1036 gcctatcaaa gacctttgt gtgtgtgtgt gc                                  1068

<210> SEQ ID NO 12
<211> LENGTH: 289
<212> TYPE: PRT
<213> ORGANISM: Sus scrofa

<400> SEQUENCE: 12

Met Pro Gln Glu Gln Tyr Thr His His Arg Ser Thr Met Pro Ser Ser
1               5                   10                  15

Glu Gly Pro Gln Val Tyr Lys Val Gly Ile Tyr Gly Trp Arg Lys Arg
            20                  25                  30

Cys Leu Tyr Phe Phe Val Leu Leu Leu Met Ile Leu Ile Leu Val Asn
        35                  40                  45

Leu Ala Met Thr Ile Trp Ile Leu Lys Val Met Asn Phe Thr Ile Asp
    50                  55                  60

Gly Met Gly Asn Leu Arg Ile Thr Glu Lys Gly Leu Lys Leu Glu Gly
65                  70                  75                  80

Asp Ser Glu Phe Leu Gln Pro Leu Tyr Ala Lys Glu Ile Gln Ser Arg
                85                  90                  95

Pro Gly Asn Ala Leu Tyr Phe Lys Ser Ala Arg Asn Val Thr Val Asn
            100                 105                 110

Ile Leu Asn Glu Gln Thr Lys Val Leu Thr Gln Leu Ile Thr Gly Pro
        115                 120                 125

Asn Ala Ile Glu Ala Tyr Gly Lys Lys Phe Glu Val Lys Thr Val Ser
    130                 135                 140

Gly Lys Leu Leu Phe Ser Ala Asp Asn Asn Glu Val Val Gly Ala
145                 150                 155                 160

Glu Arg Leu Arg Val Leu Gly Ala Glu Gly Thr Val Phe Pro Lys Ser
                165                 170                 175

Ile Glu Thr Pro Asn Val Arg Ala Asp Pro Phe Lys Glu Leu Arg Leu
            180                 185                 190

Glu Ser Pro Thr Arg Ser Leu Val Met Glu Ala Pro Lys Gly Val Glu
        195                 200                 205
```

```
Ile Asn Ala Glu Ala Gly Asn Met Glu Ala Thr Cys Arg Thr Glu Leu
    210                 215                 220
Arg Leu Glu Ser Lys Asp Gly Glu Ile Lys Leu Asp Ala Ala Lys Ile
225                 230                 235                 240
Lys Leu Pro Arg Leu Pro His Gly Ser Tyr Thr Pro Ala Gly Thr Arg
                245                 250                 255
Gln Lys Val Phe Glu Ile Cys Val Cys Ala Asn Gly Arg Leu Phe Leu
            260                 265                 270
Ser Gln Ala Gly Thr Gly Ser Thr Cys Gln Ile Asn Thr Ser Val Cys
            275                 280                 285
Leu

<210> SEQ ID NO 13
<211> LENGTH: 1064
<212> TYPE: DNA
<213> ORGANISM: Sus scrofa
<220> FEATURE:
<221> NAME/KEY: CDS
<222> LOCATION: (77)..(223)

<400> SEQUENCE: 13
ttccagcctc tccacacacg cctcctggac tgtgcggggt tctcaccagc cgctttgtgc      60
gaagaagaca agagag atg cct cag gaa cag tac aca cac cac cgg agc acc    112
               Met Pro Gln Glu Gln Tyr Thr His His Arg Ser Thr
                 1               5                  10 atg ccc agc tcc gag ggg cca cag gta tac aaa gta ggg att tac ggc      160
Met Pro Ser Ser Glu Gly Pro Gln Val Tyr Lys Val Gly Ile Tyr Gly
         15                  20                  25 tgg cgg aaa aga tgc ttg tat ttc ttt gtc cta ctc ctg atg att tta      208
Trp Arg Lys Arg Cys Leu Tyr Phe Phe Val Leu Leu Leu Met Ile Leu
     30                  35                  40 ata ctg gtg tgg cca tgaccatctg gattctcaaa gtcatgaact tcacaattga      263
Ile Leu Val Trp Pro
45 tggaatggga aacttgagaa tcacagaaaa aggtctaaag ttagaaggag actcagaatt    323 cctacaacct ctgtacgcca agaaatcca gtcccgacca ggtaatgccc tgtacttcaa      383 atctgccaga atgttactg tgaacatcct caatgaacag actaaagtgc taactcagct      443 gataacaggt ccaaatgcca tagaagctta tggcaaaaag tttgaagtaa agacggtttc    503 tggaaaattg ctcttctctg cagataacaa tgaagtcgta gtgggagctg aaagattgag    563 agttttagga gcagagggca cagtgttccc taaatctata gagacaccta atgtcagggc    623 agaccccttc aaggaactaa ggttggaatc ccccacccgg tctctggtga tggaagcccc    683 aaaaggagta gaaataaatg cagaagccgg caatatggaa gccacctgca gaacagagct    743 gagactggag tccaaagatg gagagattaa gttagatgct gcgaaaatca aactacccag    803 attgcctcac ggatcctaca cacccgcggg aacgaggcag aaggtcttcg agatctgcgt    863 ttgtgccaac gggagattat tcctgtcaca ggcaggaact ggttccactt gtcagataaa    923 cacaagtgtc tgcctgtgag agactatcca tagtggacac tgtcgcagca taaaggcctt    983 ttttggcttt agccctggc tgccagctat ttttactata acacagaaag cctatcaaag   1043 accttttgtg tgtgtgtgtg c                                             1064

<210> SEQ ID NO 14
<211> LENGTH: 49
<212> TYPE: PRT
```

<213> ORGANISM: Sus scrofa

<400> SEQUENCE: 14

Met Pro Gln Glu Gln Tyr Thr His His Arg Ser Thr Met Pro Ser Ser
1               5                   10                  15
Glu Gly Pro Gln Val Tyr Lys Val Gly Ile Tyr Gly Trp Arg Lys Arg
            20                  25                  30
Cys Leu Tyr Phe Phe Val Leu Leu Leu Met Ile Leu Ile Leu Val Trp
        35                  40                  45
Pro

<210> SEQ ID NO 15
<211> LENGTH: 2047
<212> TYPE: DNA
<213> ORGANISM: Sus scrofa

<400> SEQUENCE: 15

| | | | | |
|---|---|---|---|---|
| gctcaacatc | aaaaaagcca | acaacccaat | tgaaaaatgt | gcagaagacc | cgaatagaca | 60 |
| tttccgtaaa | gaagatatat | acatagccaa | ctggaacatg | aaaaaaatgc | tcaatatcac | 120 |
| tattagagaa | atgcaaatca | aaacggcact | gagatgccac | ctcacacgag | tcagaatggc | 180 |
| catcatcaac | aagttaacaa | ataaaaaatg | caggagaggg | tgtggaaaaa | agggtaccct | 240 |
| ccttcatcgt | tggtgggaat | ggaaattggt | acaaccacta | tggaaaacag | taaggaggta | 300 |
| cctcagaaaa | ctaaatatag | aactaccata | tatatgatcc | agcaatccca | ctcctgggca | 360 |
| tatatctgga | caaaactttc | atcaaaaaaa | tacatgcaac | cctgtattca | ctgcagaact | 420 |
| attcacaata | gccaagacat | ggaaacaacc | taaatgtcca | ttgatggatg | aatggattga | 480 |
| gaagatgtgg | tgtatataca | caatggaata | ctactcaacc | ataaaaacaa | caaaataagg | 540 |
| ccatttgcag | caacgtggat | ggaactggag | actctcatac | taagtgaagt | aagtgagaaa | 600 |
| gaaagataga | gtatatcact | tatatttgga | atctaatata | tggcacaaat | gaacctatct | 660 |
| acagaaaaga | aacaaactca | tggagttaga | aaacagacct | gtggttgtca | agcagtaggg | 720 |
| gaagggagtg | ggatggactg | ggagtttggg | gttagtagat | gcaaactatt | gtatttggag | 780 |
| tggataagca | atgagatcct | gctgtatagc | acagggaact | ctatctagtc | acttgtgatg | 840 |
| gaacatgatg | gaggataatg | taagaaaaag | aatatgtatg | tgtatggttg | ggtcactttg | 900 |
| ctgtacaata | atcatttgta | aatcaattat | aatagaaaaa | ataaataaa | attgatctca | 960 |
| ctctccccta | atcactttta | actagttcat | tcctcccatt | agcctgcaag | ctcctgggag | 1020 |
| gcatgttcac | acctttcttg | acgttgagcc | tttaatgttt | attttaaaaa | tgtgttggta | 1080 |
| agaattggaa | ttgtcttact | cataaggatt | acttgagagg | gtagtgagtt | ttctatcaag | 1140 |
| caaagcattt | aagcaaaagc | tatgactttt | tgaagattcc | tgagtcaagg | gaggcttaat | 1200 |
| tcagcacccc | tttgagtact | ggaatggagg | gaatatcaga | attgttactt | tgccattga | 1260 |
| atttctgcca | gtacaaaatg | attacatttg | agacaatttt | acaccccaaa | tgaagtgcct | 1320 |
| aagtagtaat | attataccac | cacaatgaac | tgctgggatt | aatttattgt | ctcagctaaa | 1380 |
| ttccaaattt | tatgctcaga | acttcgtctc | ccttgcaaag | atgttgggat | tctaggaatc | 1440 |
| atttggaaga | tggcttcctg | caggtcccag | ttctcccgtg | atatgtatgt | gggtgtctca | 1500 |
| gcgcacacta | tgagagatgt | ctgcatgaaa | taagggggct | cctgcaagtg | tccagaggag | 1560 |
| cccctttgt | ccagagggaa | aagattttta | gcgtcgtaag | gagggtggac | acgtacagac | 1620 |
| agcagccagc | catatctctt | catcagttga | ttttttccat | tctcctttc | tctctctcag | 1680 |

```
cagtttaatg tgagtgcttc tctctcacct cgtttatttc agatgcctca ggaacagtac    1740
acacaccacc ggagcaccat gcccagctcc gaggggccac aggtatacaa agtagggatt    1800
tacggctggc ggaaaagatg cttgtatttc tttgtcctac tcctgatgat tttaatactg    1860
gtgaacttgg ccatgaccat ctggattctc aaagtcatga acttcacaat tgtaagtaaa    1920
accctaacaa attttttatc tctccttagg ggaagggaaa gcatgaggcg agaagaaggt    1980
atgtggaaag tgatggtagt aggattcaaa ataacctgca tcttggtgtt ttgatgaaaa    2040
ggaaaaa                                                              2047

<210> SEQ ID NO 16
<211> LENGTH: 188
<212> TYPE: DNA
<213> ORGANISM: Sus scrofa

<400> SEQUENCE: 16
gctcaacatg gccatgacca tctggattct caaagtcatg aacttcacaa ttgtaagtaa      60
aaccctaaca aattttttat ctctccttag gggaagggaa agcatgaggc gagaagaagg     120
tatgtggaaa gtgatggtag taggattcaa ataacctgc atcttggtgt tttgatgaaa     180
aggaaaaa                                                              188
```